US009046882B2

(12) United States Patent
Bartee et al.

(10) Patent No.: US 9,046,882 B2
(45) Date of Patent: Jun. 2, 2015

(54) NONLINEAR MODEL PREDICTIVE CONTROL OF A BATCH REACTION SYSTEM

(75) Inventors: James Bartee, Stilesville, IN (US); Maina A. Macharia, Round Rock, TX (US); Patrick D. Noll, Richardson, TX (US); Bijan Sayyar-Rodsari, Austin, TX (US); Michael E. Tay, Georgetown, TX (US)

(73) Assignee: ROCKWELL AUTOMATION TECHNOLOGIES, INC., Mayfield Heights, OH (US)

( * ) Notice: Subject to any disclaimer, the term of this patent is extended or adjusted under 35 U.S.C. 154(b) by 610 days.

(21) Appl. No.: 12/827,876

(22) Filed: Jun. 30, 2010

(65) Prior Publication Data

US 2012/0003623 A1    Jan. 5, 2012

(51) Int. Cl.
 *G05B 21/00* (2006.01)
 *G05B 17/02* (2006.01)

(52) U.S. Cl.
 CPC ....................................... *G05B 17/02* (2013.01)

(58) Field of Classification Search
 CPC ....................................................... G05B 17/02
 USPC ........................... 700/8, 266, 268; 702/31, 32
 See application file for complete search history.

(56) References Cited

U.S. PATENT DOCUMENTS

| | | | |
|---|---|---|---|
| 2008/0103747 A1 | 5/2008 | Macharia et al. | |
| 2008/0103748 A1 | 5/2008 | Axelrud et al. | |
| 2008/0104003 A1 | 5/2008 | Macharia et al. | |
| 2008/0108048 A1 | 5/2008 | Bartee et al. | |
| 2008/0109100 A1 | 5/2008 | Macharia et al. | |
| 2008/0109200 A1 | 5/2008 | Bartee et al. | |
| 2008/0167852 A1 | 7/2008 | Bartee et al. | |
| 2009/0235716 A1 | 9/2009 | Stephenson et al. | |
| 2009/0240603 A1 | 9/2009 | Stephenson et al. | |
| 2009/0326695 A1 | 12/2009 | Macharia et al. | |
| 2010/0082139 A1 | 4/2010 | Macharia et al. | |
| 2010/0082140 A1 | 4/2010 | Macharia et al. | |
| 2010/0082166 A1 | 4/2010 | Macharia et al. | |
| 2010/0082312 A1 | 4/2010 | Macharia et al. | |

OTHER PUBLICATIONS

Receding Horizon Control for Temporal Logic Specifications, Wongpiromsarn et al. HSCC '10 Proceedings of the 13th ACM international conference on Hybrid systems: computation and control pp. 101-110 Apr. 12-15, 2010.*

(Continued)

*Primary Examiner* — Shogo Sasaki
(74) *Attorney, Agent, or Firm* — Fletcher Yoder P.C.

(57) ABSTRACT

The present invention provides novel techniques for controlling batch reaction processes. In particular, a parametric hybrid model may be used to parameterize inputs and outputs of batch reaction processes. The parametric hybrid model may include an empirical model, a parameter model, and a dynamic model. Critical quality parameters, which are correlated with, but not the same as, end-of-batch quality values for the batch reaction processes may be monitored during cycles of the batch reaction processes. The quality parameters may be used to generate desired batch trajectories, which may be used to control the batch reaction processes during the cycles of the batch reaction processes.

8 Claims, 13 Drawing Sheets

(56) References Cited

OTHER PUBLICATIONS

Nonlinear Controllers for Trajectory Tracking in Batch Processes, Carrier et al. Compurers them. Engng vol. 13, No. I/2, pp. 73-82, 1989.*

A Parametric Hybrid Model used for Multidimensional Object Representation, Vaerman et al. Image Processing, 1999. ICIP 99. Proceedings. 1999 vol. 1 pp. 163-167.*

* cited by examiner

US 9,046,882 B2

NONLINEAR MODEL PREDICTIVE CONTROL OF A BATCH REACTION SYSTEM

BACKGROUND

The present invention generally relates to the field of model predictive control of production processes. More particularly, the present invention relates to systems and methods for model predictive control of a batch reaction process of a production process.

BRIEF DESCRIPTION

Batch reaction systems occur in chemical, biochemical, pharmaceutical, water treatment, and many other industrial applications. These systems as compared to continuous process systems are un-steady-state with respect to time or batch progression, whereas continuous process systems run constantly, without typical batch stages of preparation, initiation/start-up, production, emptying, and cleaning. Batch systems are inherently time-variant systems, whereas continuous systems are conceptually time-invariant (e.g., the model input/output relationship is independent of time). Classical model predictive control is designed for continuous production operations where operating targets, process relationships, and operating limits can be modeled with continuous process models of linear or nonlinear relationships. Batch reaction systems frequently have operating phases within the above described production operation including feeding (adding of feedstock), initiation, lag phases or acclamation to operating condition changes, production, exhaustion, termination, and unproductive phases. Each of these potential batch processing phases that exist in a batch reaction system have varying process relationships (e.g. nonlinear) that transition continuously from one phase to the next over time or batch progression. Therefore classical model predictive control (MPC) solutions must be adjusted to enable predictive control solutions even though the opportunities to increase performance exist equally in batch and continuous process operations.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
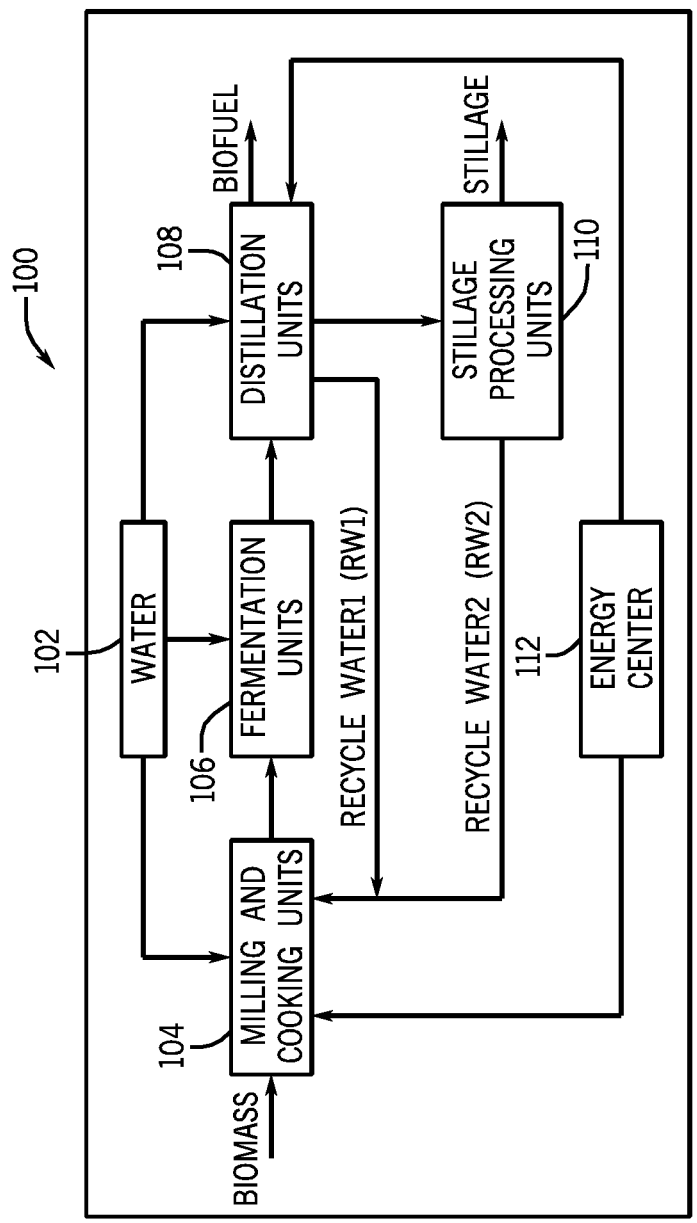
FIG. 1 illustrates one example of a processing plant having batch reaction processes.

Turning now to the drawings, FIG. 1 is an exemplary high-level design of a production plant or process having batch reaction processes. In particular, the illustrated production plant is a biofuel production plant. However, other types of production plants (e.g., chemical, biochemical, pharmaceutical, water treatment, and so forth) having batch reaction processes may be used in conjunction with the embodiments described herein. FIG. 1 illustrates how biomass or other batch feedstock is processed through several stages to produce a batch reaction product and possibly one or more co-products. Batch reactor feedstock can be processed prior to the batch reactor system in various ways and the critical nature of such pre-processing is that the focus is to enable presentation of the reaction feedstock in an optimal way to target higher yields (e.g., higher conversion of feedstock into product) at a design, rapid reaction rate. Controls of batch feedstock(s) (e.g., there may be more than one critical reaction feedstock component) revolves around making feedstock available for the catalyst or biologic conversion agent (e.g., enzyme, organism, and so forth) so that it is readily processed. This includes control of concentration, temperature, specificity (e.g., including orientation, isomer, and so forth) or conversion (e.g., of starches to dextrin or ethylene to vinyl). The output (i.e., the batch reactor feedstock(s)) of the batch feedstock processing units 104 (e.g., milling and cooking units 104 in a biofuel production process) is then sent to a batch reactor process, where one or more reaction units 106 (e.g., fermentation units 106 in a biofuel production process) operate to convert the feedstock produced by the feed preparation process.

Figure 2:
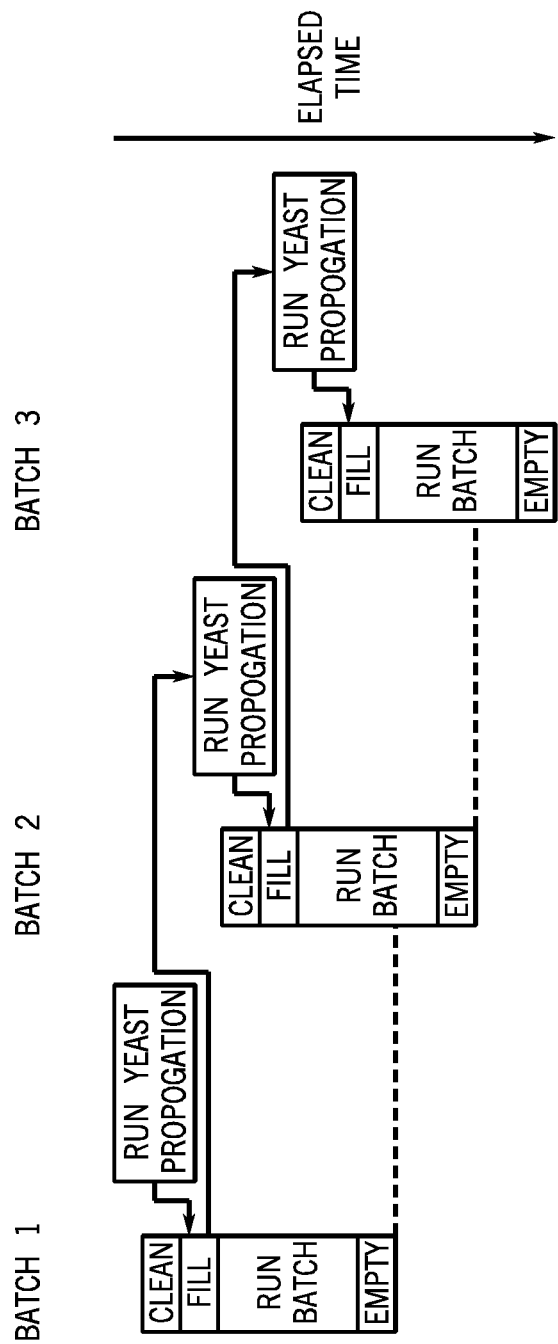
FIG. 2 illustrates a simplified processing flow schematic of three parallel batch reaction processes with staggered start times.
Figure 3:
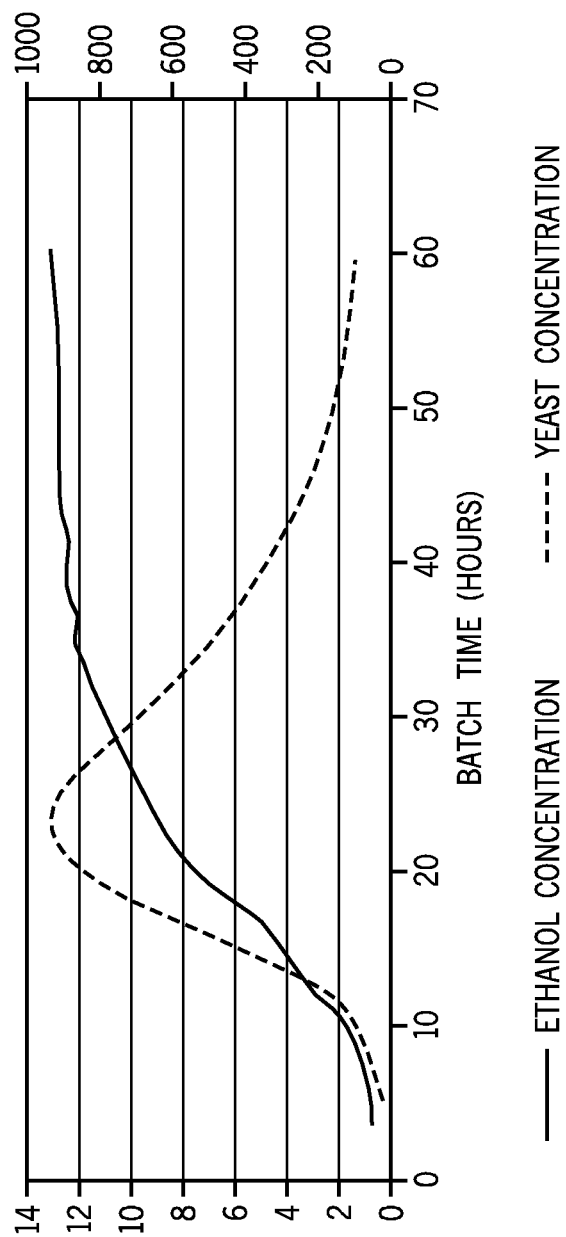
FIG. 3 illustrates an exemplary plot of active yeast and ethanol concentrations as a function of batch time.

As FIG. 1 indicates, the batch reaction process may require additional water 102 or other solvent or carrier compounds to control the consistency of material to the batch reaction units (also referred to herein as a fermenter or a fermentation tank, where fermentation is specific to biologic conversion processes, although these concepts are generally valid in any time-variant/batch process operation, be it chemical or biological). Feedstock is converted by catalysts or bio-conversion agents into a product compound, by-products (e.g., carbon dioxide, dimers, trimers, and smaller chains of polymer feedstock), and non-fermentable biomass (solids), in the batch reaction units 106. The described reaction process is generally a batch reaction process with multiple reactors in parallel. The batch start times are staggered as shown in FIG. 2 in order to optimize the size of holding tanks and smooth out the flow of feedstock to the batch reaction process and the flow of products and by-products as output from the batch reaction process. FIG. 3 indicates an exemplary plot of active yeast and ethanol concentrations as a function of batch time for a fermentation batch. Again, the embodiments described herein relating to fermentation processes are only one type of batch reaction process that may benefit from the embodiments described herein. For example, other exemplary batch reaction processes associated with chemical, biochemical, pharmaceutical, water treatment, and many other industrial applications may utilize the model predictive control techniques described herein. These applications include batch polymer reactors such as PVC production, batch pulp processing such as batch kamyr digesters, and other batch bioprocesses such as pharmaceutical production, among others.

Returning now to FIG. 1, the output from the batch reaction units 106 is sent to a refining process such as distillation to purify and isolate products from by-products and solvent (e.g., one or more distillation units 108 to separate biofuel from water, carbon dioxide, and non-fermentable solids). Many types of post-reactor processing examples may be used such as distillation, drying, molecular sieves, and centrifugation, among others. The finalized product is then processed to ensure it is ready for targeted end uses, and this can include adding other reagents, tableting, managing end-dosing, and so forth. Distillation units 108 separate the product from water or other solvents. Water or other solvents 102 may be used for heat and separation, and the condensed solvent or recovered, unconverted feedstock may be recycled (RW1) back to the feed preparation units 104, as shown in FIG. 1. Residuals (non-fermentable or reacted feedstock and catalyst or bioagent residue), the heaviest output of the distillation or other first-stage post-batch reaction processing units, may be sent to other secondary processing units for further development of co-products from the batch production process.

Secondary processing units 110 (e.g., stillage processing units 110) separate additional solvent or water from the unreacted feedstock and recycle this solvent (RW2) back to the feed preparation units 104. There are a number of secondary processing options: drying, centrifugation, flash vessels, evaporation, further reaction units, and so forth. Note that an energy center 112 supplies energy to various of the processing units, e.g., the milling and cooking units 104, the distillation 108 and mole-sieve units, evaporation, drying or other processing units. The energy center 112 may constitute a thermal oxidizer unit and heat recovery steam generator that destroys volatile organic compounds (VOCs) and provides steam to the evaporators, distillation units 108, cooking system units (e.g., in 104), or dehydration units. The energy center 112 may be the largest source of heat in a batch processing plant.

In conventional batch processing plants, properties such as temperature or product quality are controlled with control systems utilizing traditional control schemes such as temperature, pressure, level, and/or flow control schemes, which may include proportional integral derivative (PID), cascade, feed-forward, and/or constraint control schemes, among others. The systems may be open or closed. An open loop system is a system that responds to an input, but the system is not modified because of the behavior of the output. An open loop system receives process input, and generates process output, with no feedback from output back to input. Open loop systems are only defined by the inputs and the inherent characteristics of the system or process. In the batch production processes, the system may comprise the entire batch processing plant, one process section of the plant, such as the frequently continuous feed processing units, or a controller for a variable in a process such as the temperature of the preheat or batch reactor units. In a closed loop system, the inputs are adjusted to compensate for changes in the output, where, for example, these changes may be a deviation from the desired or targeted measurements. The closed loop system senses the change and provides a feedback signal to the process input. The closed loop system receives process input and generates process output, but where at least a portion of the output is provided back to the input as feedback. Process units in the batch processing system may be closed loop systems if they need to be regulated subject to constraints such as product quality, energy costs, or process unit capacity.

Modern plants apply traditional and advanced controls to regulate complex processes to achieve a specific control objective. Traditional PID controllers and other control systems such as ratio controls, feed-forward controls, and process models may be used to control batch production processes (a PID is a control algorithm or device that uses three basic feedback control modes to act on a deviation from its control objective: proportional action control (P), integral action (I), and derivative (D) rate of change action). A DCS (distributed control system) will have many traditional control schemes set up to control the process unit variables at the local control level.

Most batch production facilities pre-process feedstock or other reactor additives (e.g., catalysts, additional ingredients, and so forth), and mix this combined feedstock base with solvent or water from a variety of sources and quality. An operating challenge is to provide a steady quality and concentration of feed to the batch processing units. However, due to variability in feedstock amounts, flow rates, concentrations, preprocessing efficiencies, or additive ingredient quality, the batch reactor output varies dramatically and the process may operate sub-optimally due to this large variability. Batch reactor end concentrations of product may vary plus or minus 10% or more.

Batch processing plants may be implemented to provide some information to plant operators to enable them to increase or decrease the flows of feedstock and additive concentrations to batch reactor vessels. Plant operators may monitor the target feed quality and percent concentrations in the reactor feed and run the pre-processing plants to achieve a target percent ingredient/feedstock so that each batch is started with a rough approximation of the target concentrations and each batch runs over a specific time period in an attempt to achieve an output with approximately the design target percent of product. In addition, a recycle flow rate on solvent or feedstock or other ingredients may be managed to maintain tank inventory levels within safe operating limits, while providing sufficient fresh solvent or other ingredients to mix with feedstock to fill a batch reactor within a targeted time period (i.e. fill a vessel of 180,000 gallons in 15 hours so that the fill rate would be 600 gallons per minute). In addition, levels of various ingredient sources tend to increase or decrease, and operators or level controllers may adjust flows to regain targeted levels. In general, these applications may be controlled with flow, level, or speed controllers (e.g., regulatory level controllers).

Two additional calculated parameters are also important to plant operators. The first parameter is percent recycle, which is the fractional percentage of recycled solvent, unconverted feedstock or other recoverable ingredients. Percent recycle may be managed manually to both maintain rough inventories and to operate within a range of fractional percent fresh material. It is important to manage the fractional percent fresh material, because the recycled material may contain both residual useful additives along with reactor waste products or inhibition by-products from previous batches. Too little or too much recycle can be a problem for batch reactor productivity.

The second parameter is batch reactor inventory, which is a totalized inventory across the filling, draining, and reacting batch vessels and key auxiliary equipment. If this total inventory level is held within an acceptably stable band, the front plant section (i.e., the raw material pre-processing, and batch reaction processes) can be managed to match the back finishing plant sections (i.e., the distillation, drying, evaporation, or tableting/packaging processes) across all batch sequentially operated reaction vessels. If totalized batch volume is constant, then filling is balanced with draining across multiple parallel batch reaction vessels.

A batch processing production plant may require numerous adjustments, e.g., on a minute-to-minute basis, in response to changes and shifting constraints if the plant process is to operate in an optimal manner. Due to this complexity, human operators are not capable of actively optimizing a batch or an integrated batch and continuous production process. Consequently, operators generally operate a plant in a less efficient operating mode. Thus, improved systems and methods for batch processing are desired.

Figure 4A:
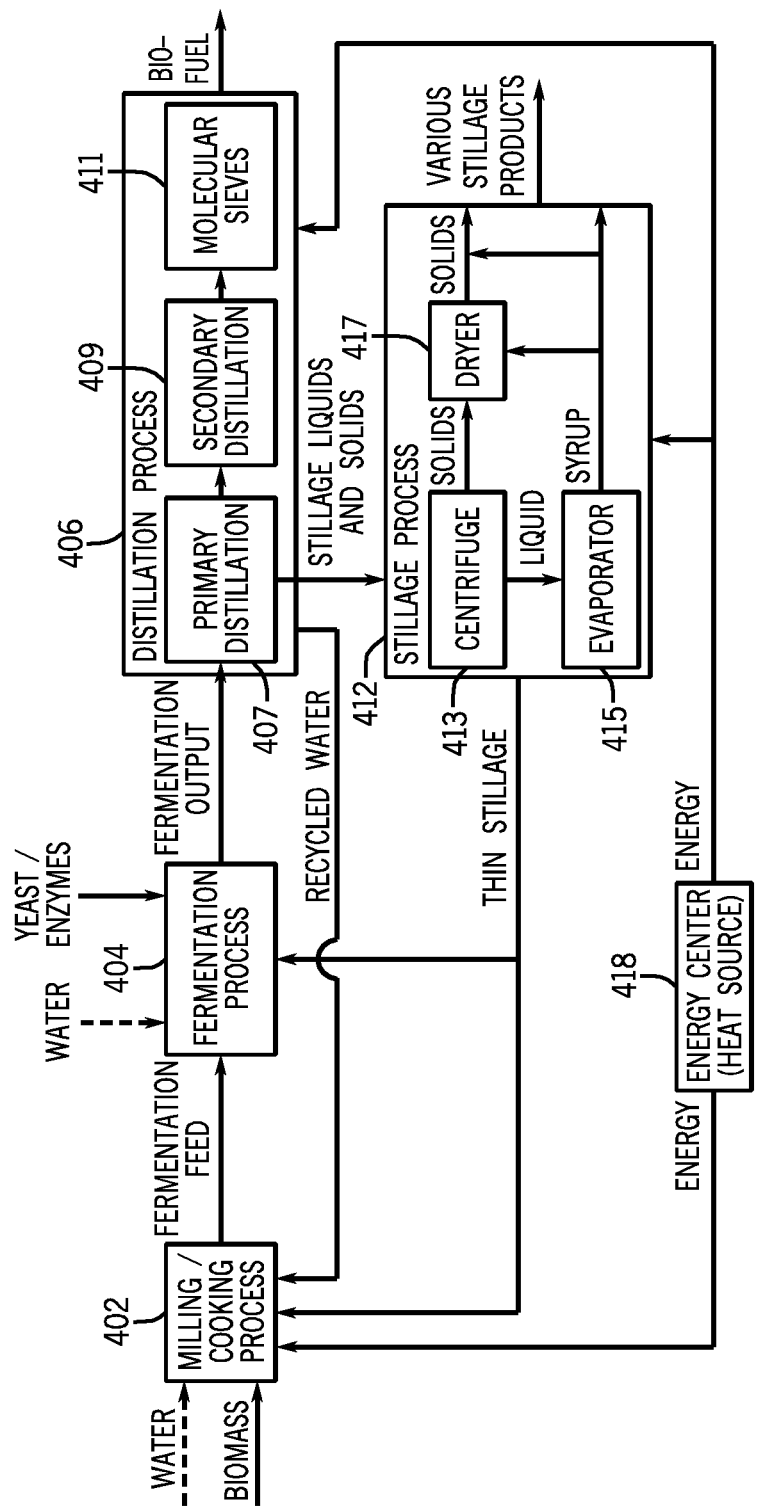
FIG. 4A illustrates an exemplary high-level processing flow schematic of plant sections of a biofuel processing plant.

FIG. 4A illustrates an exemplary high-level processing flow schematic of sub-processes of a batch production process, according to one embodiment. It should be noted that the particular components and sub-processes shown are meant to be exemplary only, and are not intended to limit embodiments of the invention to any particular set of components or sub-processes.

As FIG. 4A indicates, a pre-processing sub-process 402 (e.g., a milling/cooking sub-process 402) may: receive solvent (e.g., water), feedstock (e.g., biomass), energy (electrical and/or thermal), and recycled solvent or recovered unconverted feedstock; mill or otherwise process the feedstock; pre-cook or pre-heat the batch feed mixture; and output a feedstock blend (also referred to as a batch reactor feed blend or a feed slurry) to a batch reactor sub-process 404 (e.g., a fermentation sub-process 404). The batch reactor sub-process 404 may receive the feed slurry, recycled solvent, catalyst, and recycled unconverted feedstock. The batch reactor sub-process 404 may also receive additional fresh solvent (not recycled). The mixture is reacted, and the reaction products output to a distillation or other post-reaction sub-process 406. The post-reaction sub-process 406 may: receive the reactor products, remove water or other solvent and by-products from the batch reactor products in a one to multi-step process (e.g., primary distillation 407, secondary distillation 409, and/or molecular sieves 411 (or dryers, evaporators, others)), recycle solvent removed from the batch reactor products to the pre-processing sub-process 402, output the by-products to a by-product processing sub-process 412 (e.g., a stillage process 412), and output batch reaction products. The by-product processing sub-process 412 may: receive the residual solvent and by-products, process and purify the by-product (utilizing one or more of centrifuges 413, other dryers 417, and/or evaporators 415) to produce and output various by-products, and recycle recovered solvent to the batch reaction sub-process 404 and the pre-processing sub-process 402. An energy center 418 may provide electric power and heat (steam) to the various sub-processes as shown in FIG. 4A.

Figure 4B:
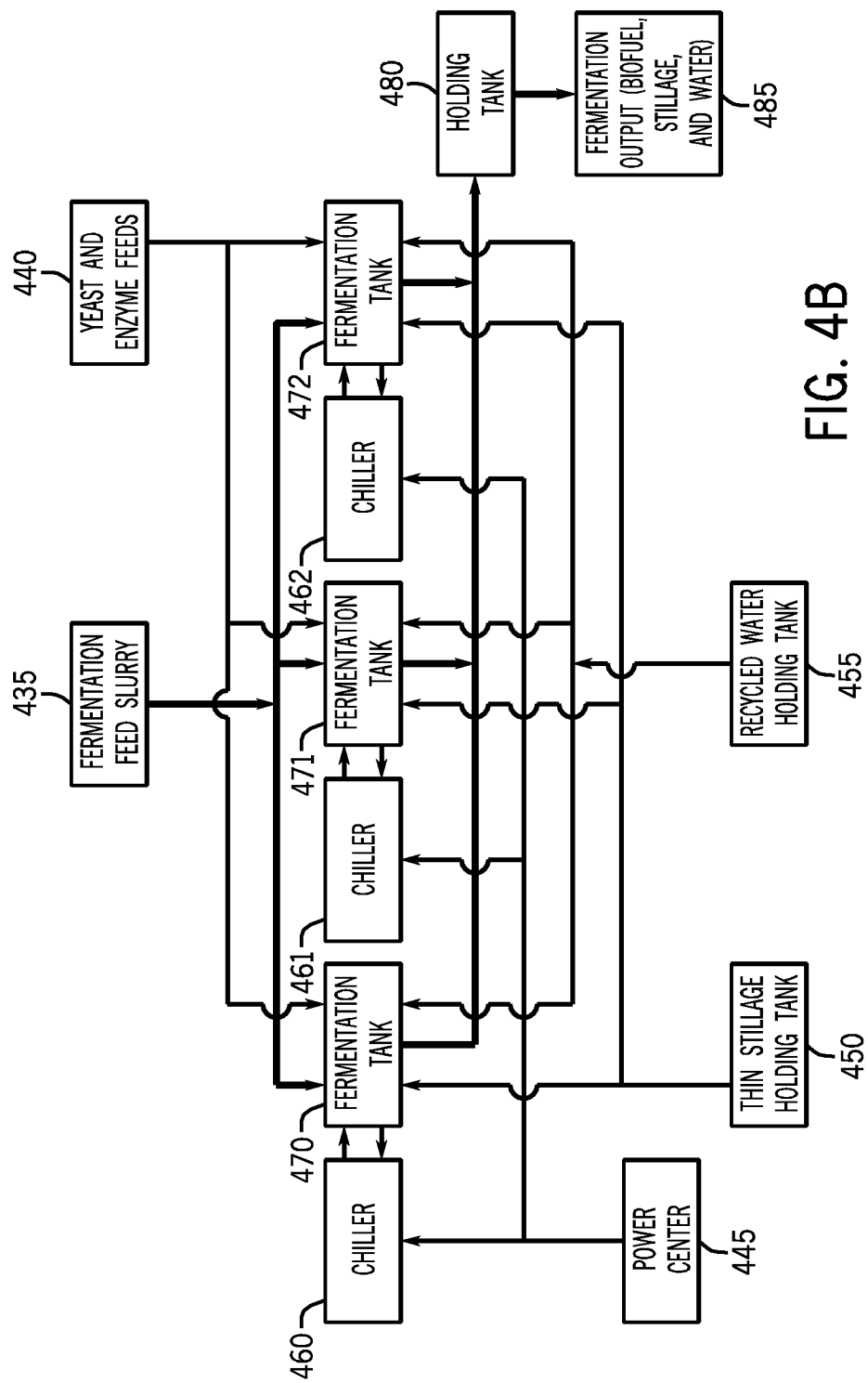
FIG. 4B is a high-level block diagram of a batch reaction process.

FIG. 4B illustrates an exemplary high-level processing flow schematic of a batch reaction process (e.g., fermentation process 404 in FIG. 4A) of a biofuel production process, according to one embodiment. It should be noted that the particular components or sub-processes shown are meant to be exemplary only, and are not intended to limit embodiments of the invention to any particular set of components or sub-processes.

The fermentation process equipment may include a single fermentation tank, a few fermentation tanks (e.g., the three tanks 470-472 shown in FIG. 4B), or many fermentation tanks, depending on the size of the biofuel production plant. One or more chillers 460-462 may be coupled to the fermentation tanks and provide cooling to the fermenting slurry inside the fermentation tanks through heat exchangers. Electric power may be provided to the chillers 460-462 (and various pumps, controllers, and sensors—not shown in FIG. 4B) from an energy center 445.

The fermentation process, like other batch reaction processes, is typically a batch process, and each batch has a filling period, a fermentation period, and an emptying period. The fermentation period begins with the introduction of yeast to the tanks (yeast and enzyme feeds 440), and overlaps the filling period. The fermentation period may continue through a portion of the emptying period until the yeast is effectively depleted. The initiation time of a batch for each fermentation tank may be staggered, so that 1) the tanks are filling at different times in order to optimally utilize the fermentation feed slurry provided to the fermentation tanks from the milling/cooking process 402; and 2) the fermentation tanks are emptying at different times into the one or more holding tanks 480 (some embodiments may have multiple holding tanks 480) to optimize the size of the one or more holding tanks 480.

Thin stillage (impure recycled water) may be added to the fermentation tanks 470-472 from one or more thin stillage holding tanks 450. Thin stillage may be provided from the stillage process 412. Recycled water may also be added to the fermentation tanks 470-472 from one or more recycled water holding tanks 455. Recycled water may be provided from the distillation process 406. Additional water may be added from other sources as needed. The fermentation process output (biofuel, stillage, and water) 485 is sent to holding tanks for the distillation process 406.

Figure 4C:
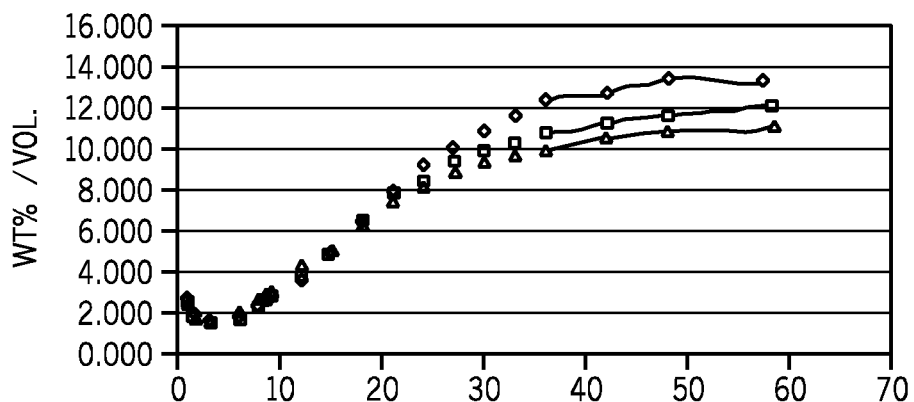
FIG. 4C illustrates an exemplary plot of product concentrations as a function of batch time for three separate fermentation batches.
Figure 4D:
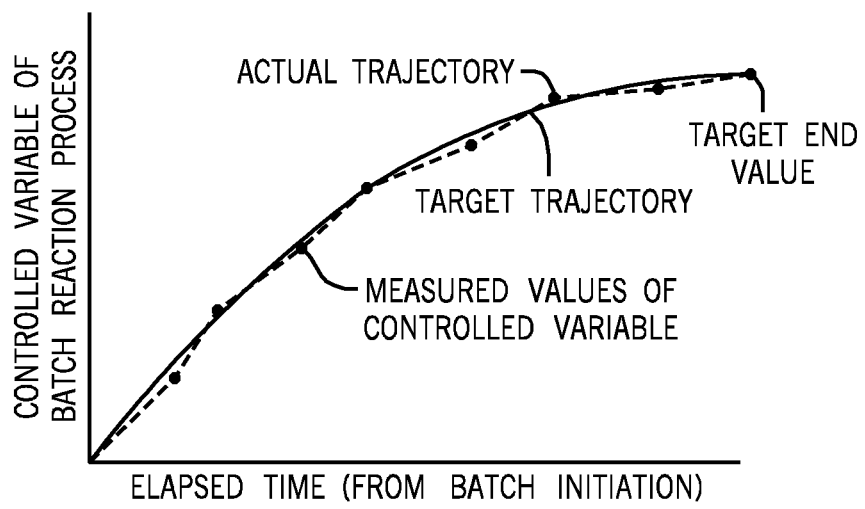
FIG. 4D illustrates an exemplary target trajectory compared to an exemplary actual trajectory for a controlled variable of a batch reaction process.

Control of the fermentation process 404 may be achieved by adjusting the values of manipulated variables of batch fermentation and monitoring the subsequent changes in one or more controlled variables of the batch fermentation. FIG. 4C illustrates one control variable (biofuel concentration) measured for several fermentation batches, and illustrates the variability of the fermentation process. FIG. 4D illustrates control of a batch reaction process to an optimized target trajectory for a controlled variable of the batch (e.g., biofuel concentration), and the actual trajectory achieved by adjusting values for the manipulated variables during the batch reaction process. For example, a fermentation process may be managed and controlled via model predictive control (MPC) utilizing a dynamic multivariate predictive model that may be incorporated as a process model in a dynamic predictive model-based controller. Model predictive control of the fermentation process (also referred to as a fermentation sub-process) of a biofuel production process is described below in more detail.

Various embodiments of systems and methods for applying model predictive control (MPC) to a biofuel production process are described below. In this approach to biofuel production, a dynamic multivariate predictive model may be incorporated as a process model in a dynamic predictive model-based controller. This MPC system may project or predict what will happen in the production process (e.g., in the near future) based on the dynamic prediction model and recent process history, including, for example, recent operating conditions or state values. This projection or prediction may be updated or biased based on received current process information, specified objectives, and/or system or method constraints. Control algorithms may be used to recursively or iteratively estimate the best current and future control adjustments on the model inputs to achieve a desired output path. Targets set on the dynamic model outputs may be compared to how that output may behave over a predictive future horizon and the best available controllable model input adjustments may be estimated to best achieve the controller targets.

It should be noted that the biofuel produced by embodiments of the methods described herein may be any biofuel generated from biomass, and that the types of biomass contemplated may be of any type desired, including, but not limited to, grains (e.g., corn, wheat, rye, rice, etc.), vegetables (e.g., potatoes, beats, etc.), canes (e.g., sugarcane, *sorghum*, etc.), and other recently living organisms and/or their bi-products.

Figure 5:
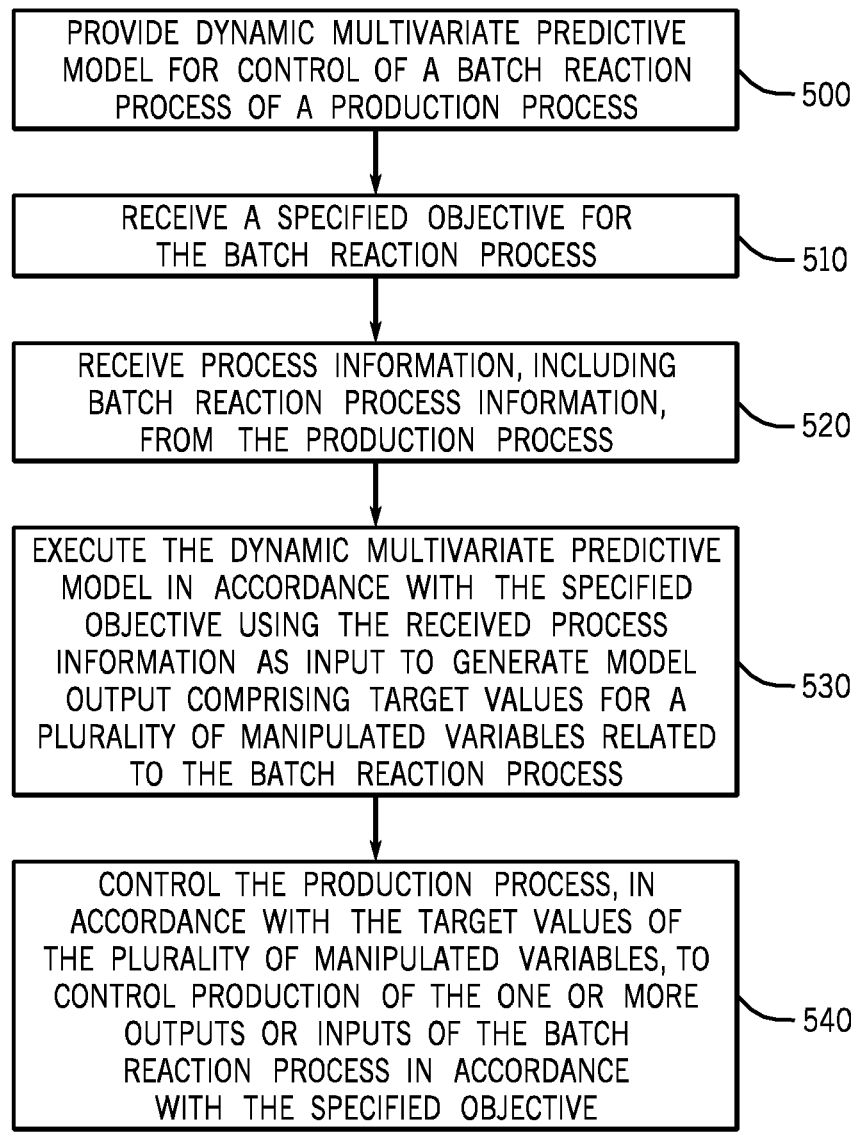
FIG. 5 is a high-level flowchart of a method for managing a fermentation process of a production process utilizing model predictive control.

FIG. 5 is a high-level flowchart of a computer-implemented method for managing a batch reaction process of a production process utilizing model predictive control (MPC). In certain embodiments, the batch reaction process may be a fermentation process of a biofuel production process. However, in other embodiments, the batch reaction process may be other processes of chemical, biochemical, pharmaceutical, water treatment, and other industrial applications. As used herein, the term biofuel refers to one or more biofuel products output from a biofuel production process. It should be noted that embodiments of the method of FIG. 5 may be used with respect to any sub-process of a biofuel production process desired (e.g., milling/cooking, fermentation, distillation, and/or stillage sub-processes), as well as combinations of such sub-processes. In various embodiments, some of the method elements shown may be performed concurrently, in a different order than shown, or may be omitted. Additional method elements may also be performed as desired.

In step 500, a dynamic multivariate predictive model (also referred to as a dynamic predictive model) of a batch reaction process of a production process may be provided. In other words, a model may be provided that specifies or represents relationships between attributes or variables related to the batch reaction process, including relationships between inputs to the batch reaction process and resulting outputs of the batch reaction process. Note that the model variables may also include aspects or attributes of other processes or sub-processes that have bearing on or that influence operations of the batch reaction process. The models may be time variant or time invariant in describing the relationship between the process inputs and the process outputs.

The model may be of any of a variety of types. For example, the model may be linear or nonlinear, although for most complex processes, a nonlinear model may be preferred. Other model types contemplated include fundamental or analytical models (i.e., functional physics-based models), empirical models (such as neural networks or support vector machines), rule-based models, statistical models, standard MPC models (i.e., fitted models generated by functional fit of data), or hybrid models using any combination of the above models.

In step 510, an objective for the batch reaction process may be received. The objective may specify a desired outcome, result, behavior, or state, of the batch reaction process, such as, for example, a desired throughput, quality, efficiency, product profile, behavior, or cost, among others. In certain embodiments, the objective may specify at least one targeted measurable attribute defining product quality for the batch reaction process (or the overall production process). Note that an objective may be a specific value, such as a specified percent solids for a fermentation feed, a specified temperature of a fermentation vat, etc., or may be a specified extremum, i.e., a maximum or minimum of an attribute, such as, for example, minimizing cost, maximizing production, etc.

It should be noted that as used herein, the terms "maximum", "minimum", and "optimum", may refer respectively to "substantially maximum", "substantially minimum", and "substantially optimum", where "substantially" indicates a value that is within some acceptable tolerance of the theoretical extremum, optimum, or target value. For example, in certain embodiments, "substantially" may indicate a value within 10% of the theoretical value. In another embodiment, "substantially" may indicate a value within 5% of the theoretical value. In a further embodiment, "substantially" may indicate a value within 2% of the theoretical value. In yet another embodiment, "substantially" may indicate a value within 1% of the theoretical value. In other words, in all actual cases (non-theoretical), there are physical limitations of the final and intermediate control element, dynamic limitations to the acceptable time frequency for stable control, or fundamental limitations based on currently understood chemical and physical relationships. Within these limitations the control system will generally attempt to achieve optimum operation, i.e., operate at a targeted value or constraint (max or min) as closely as possible.

Moreover, in certain embodiments, an objective may include multiple components, i.e., may actually comprise a plurality of objectives and sub-objectives. In certain embodiments, the objective may involve multiple variables, e.g., a ratio of variables. Moreover, in certain embodiments, there may be a global objective, e.g., maximize production or profit, and multiple sub-objectives that may in some cases be at odds with the global objective and/or one another.

In step 520, process information for the batch reaction process of the production process may be received. This information may be received from the batch reaction process, from other portions of the production process that influence the batch reaction process, and/or from other sources, e.g., a laboratory, inferred property models (that model variables that are not readily measurable), sometimes referred to as virtual online analyzers (VOAs), external systems, or any other source as desired. This information generally includes data from one or more sensors monitoring conditions of and in the batch reaction process (e.g., temperatures, pressures, flow rates, equipment settings, and so forth), although any other information germane to the batch reaction process may be included as desired (e.g., constraints to which the batch reaction process may be subject, ambient conditions of the production process, economic or market data, and so forth).

In step 530, the model may be executed in accordance with the objective for the batch reaction process using the received process information as input, to generate model output comprising target values for one or more manipulated variables related to the batch reaction process in accordance with the objective for the batch reaction process. In other words, the model may be executed with the received process information as input, and may determine target values of one or more controllable attributes of the batch reaction process in an attempt to meet the specified objective for the batch reaction process (which could be a global objective for the entire production process). For example, in an embodiment where the objective is to maximize output for the batch reaction process, the model may determine various target values (e.g., fermentation feed input flows, temperatures, pressures, and so forth) that may operate to maximize the output. As another example, in an embodiment where the objective is to minimize waste for the batch reaction process, the model may determine target values that may operate to minimize waste for the batch reaction process, possibly at the expense of total output. In a further example, the objective may be to maximize profit for the entire production process, where maximizing output and minimizing waste may be two, possibly competing, sub-objectives, e.g., included in the objective.

In certain embodiments, the execution of the model in step 530 may include executing the model in an iterative manner, e.g., via an optimizer, e.g., a nonlinear optimizer, varying manipulated variable values (which are a subset of the model inputs) and assessing the resulting model outputs and objective function, to determine values of the manipulated variables that satisfy the objective subject to one or more constraints, e.g., that optimize the sub-process subject to the constraints, thereby determining the target values for the manipulated variables.

In step 540, the batch reaction process of the production process may be controlled in accordance with the corresponding targets and objective for the batch reaction process. In other words, a controller coupled to the dynamic multivariate predictive model may automatically control various (controllable) aspects or variables of the batch reaction process according to the target values output by the predictive model to attempt to achieve the specified objective.

The method of FIG. 5 may be repeated, e.g., at a specified frequency, or in response to specified events, so that the batch reaction process may be monitored and controlled throughout a production process, or throughout a series of production processes. In certain embodiments, the period or frequency may be programmed or varied during the production process (e.g., an initial portion of a production process may have longer repetition periods (lower frequency), and a critical portion of a production process may have shorter repetition periods (higher frequency)).

In certain embodiments, a system implementing the control techniques disclosed herein may include a computer system with one or more processors, and may include or be coupled to at least one memory medium (which may include a plurality of memory media), where the memory medium stores program instructions according to embodiments of the present invention. In various embodiments, the controller(s) described herein may be implemented on a single computer system communicatively coupled to the plant, or may be distributed across two or more computer systems, e.g., that may be situated at more than one location. In this embodiment, the multiple computer systems comprising the controller(s) may be connected via a bus or communication network.

Figure 6A:
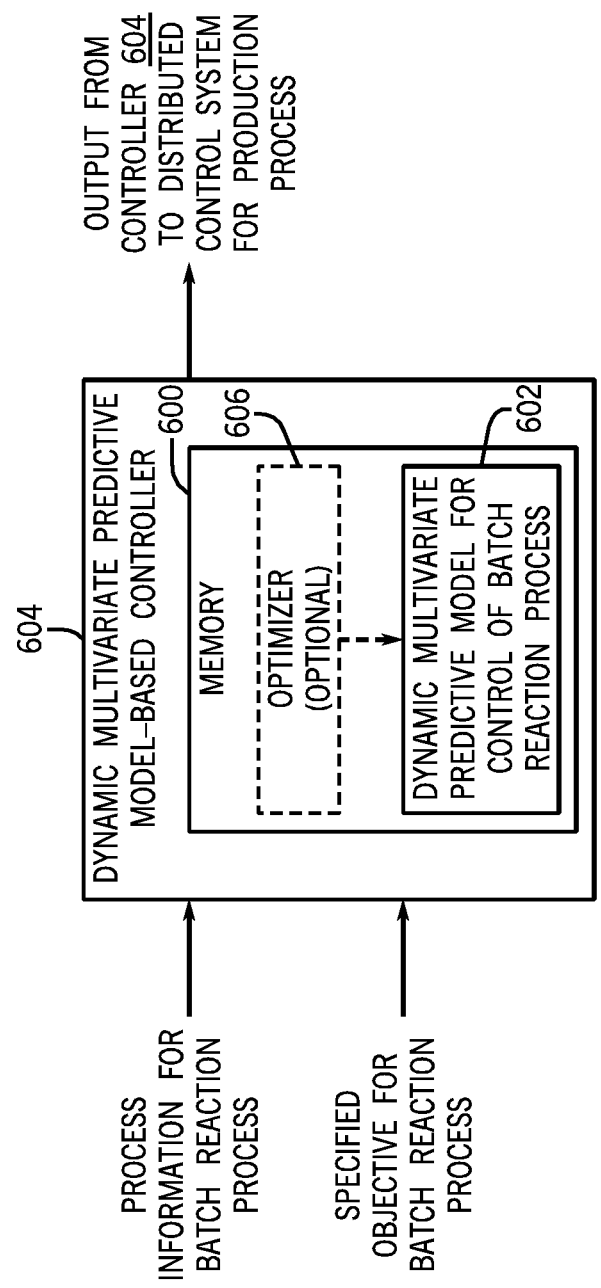
FIG. 6A is a high-level block diagram of a system for managing a batch reaction process of a production process utilizing model predictive control.

FIG. 6A illustrates an exemplary system for managing a batch reaction process of a production process, which may implement embodiments of the method of FIG. 5. The system may comprise: 1) a dynamic multivariate predictive model 602 (e.g., a predictive control model of a batch reaction process in the production process) stored in a memory medium 600; and 2) a dynamic predictive model-based controller 604 coupled to the memory medium 600. In certain embodiments, the batch reaction process may be a fermentation process of a biofuel production process. However, in other embodiments, the batch reaction process may be other processes of chemical, biochemical, pharmaceutical, water treatment, and other industrial applications.

As described above in more detail with respect to FIG. 5, the controller 604 may be operable to receive an objective for a batch process, receive process information related to the batch reaction process from the production process (possibly including information from a laboratory and/or inferred property models), execute the model in accordance with the objective for the batch reaction process using the received corresponding process information as input, to generate model output comprising target values for one or more variables related to the batch reaction process in accordance with the objective for the batch reaction process. In addition, as described above with respect to FIG. 5 in more detail, the dynamic predictive model-based controller 604 may control the batch reaction process of the production process in accordance with the corresponding targets and objective for the batch reaction process.

In certain embodiments, the controller 604 may output the target values to a distributed control system (not shown in FIG. 6A) for the production plant. In certain embodiments, the target values may include or be one or more trajectories of values over a time horizon, e.g., over a prediction or control horizon. Process information may include measurements of a plurality of process variables for the batch reaction process and other inter-related sub-processes, information on one or more constraints, and/or information about one or more disturbance variables related to the batch reaction process. Process information may be received from the distributed control system for the production plant, entered by an operator, or provided by a program. For example, in addition to values read (by sensors) from the actual process, the process information may include laboratory results, and output from inferred property models, e.g., virtual online analyzers (VOAs), among other information sources.

In certain embodiments, the memory medium 600 may be part of the controller 604. In other embodiments, the memory medium 600 may be separated from the controller 604 and connected via a bus or a communication network. In certain embodiments, the memory medium 600 may include a plurality of memory media, with different portions of the model 602 stored in two or more of the memory media, e.g., via a storage area network, or other distributed system.

Figure 6B:
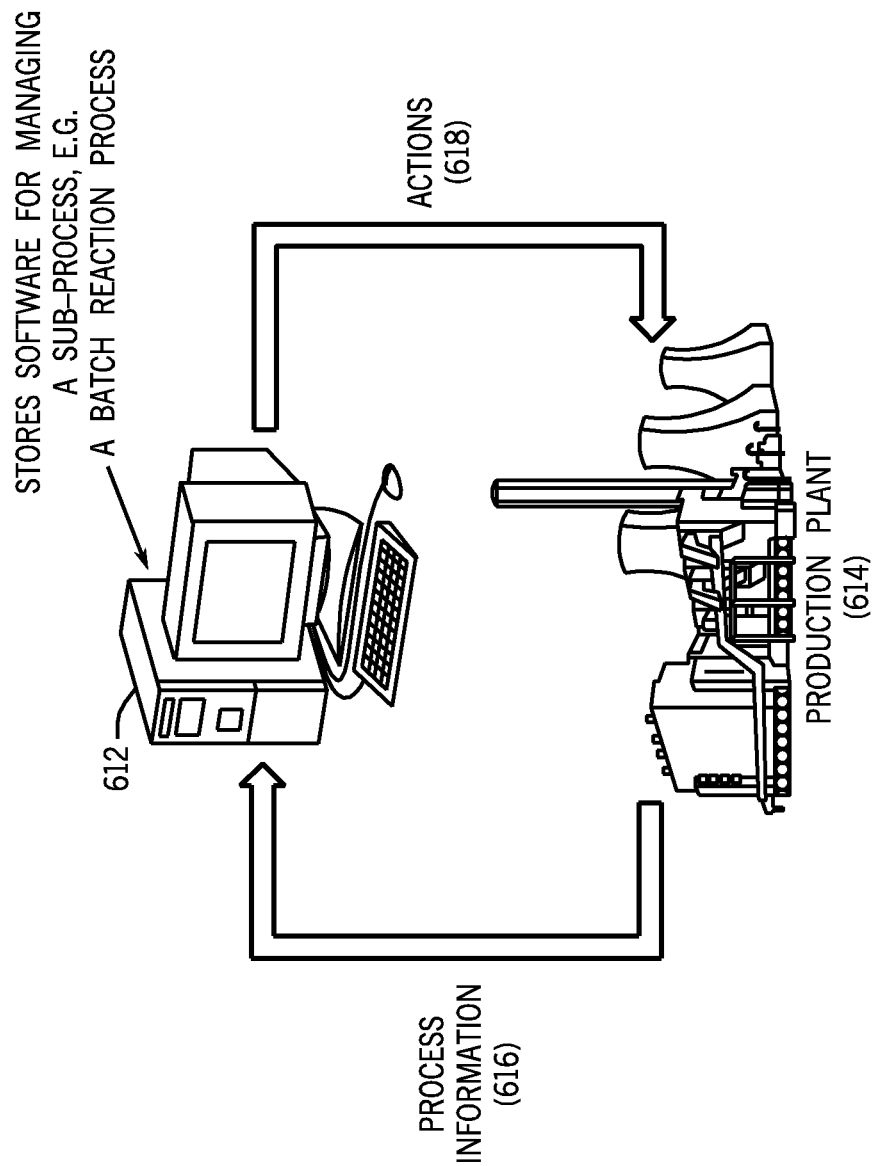
FIG. 6B is a high-level diagram of a control system for managing a production process utilizing model predictive control.

FIG. 6B illustrates a simplified view of an automated control system for a production plant 614. As shown, the system may include one or more computer systems 612 which interact with the production plant 614 being controlled. The computer system 612 may represent any of various types of computer systems or networks of computer systems, which execute software program(s) according to various embodiments of the invention. As indicated, the computer system stores (and executes) software for managing a sub-process in the production plant 614. The software program(s) may perform various aspects of modeling, prediction, optimization and/or control of the fermentation process. Thus, the automated control system may implement predictive model control of the batch reaction process in the production plant or process. The system may further provide an environment for making optimal decisions using an optimization solver, i.e., an optimizer, and carrying out those decisions, e.g., to control the production plant.

One or more software programs that perform modeling, prediction, optimization and/or control of the production plant 614 (particularly, the batch reaction processes, e.g., fermentation process) may be included in the computer system 612. Thus, the system may provide an environment for a scheduling process of programmatically retrieving process information 616 relevant to the batch reaction process of the production plant, and generating actions 618 (e.g., control actions) to control the batch reaction process, and possibly other processes and aspects of the production plant or process.

The one or more computer systems 612 preferably include a memory medium on which computer programs according to the present invention are stored. The term "memory medium" is intended to include various types of memory or storage, including an installation medium, e.g., a CD-ROM, or floppy disks, a computer system memory or random access memory such as DRAM, SRAM, EDO RAM, Rambus RAM, etc., or a non-volatile memory such as a magnetic medium, e.g., a hard drive, or optical storage. The memory medium may comprise other types of memory as well, or combinations thereof. The memory medium (which may include a plurality of memory media) preferably stores one or more software programs for performing various aspects of model predictive control and optimization. A CPU, such as the host CPU, executing code and data from the memory medium comprises a means for creating and executing the software program according to the methods or flowcharts described below. In certain embodiments, the one or more computer systems may implement one or more controllers, as noted above.

In addition, the memory medium may be located in a first computer in which the programs are executed, or may be located in a second different computer, which connects to the first computer over a network. In the latter instance, the second computer provides the program instructions to the first computer for execution. Also, the computer system(s) 612 may take various forms, including a personal computer system, mainframe computer system, workstation, network appliance, Internet appliance or other device. In general, the term "computer system" can be broadly defined to encompass any device (or collection of devices) having a processor (or processors), which executes instructions from a memory medium.

Figure 7:
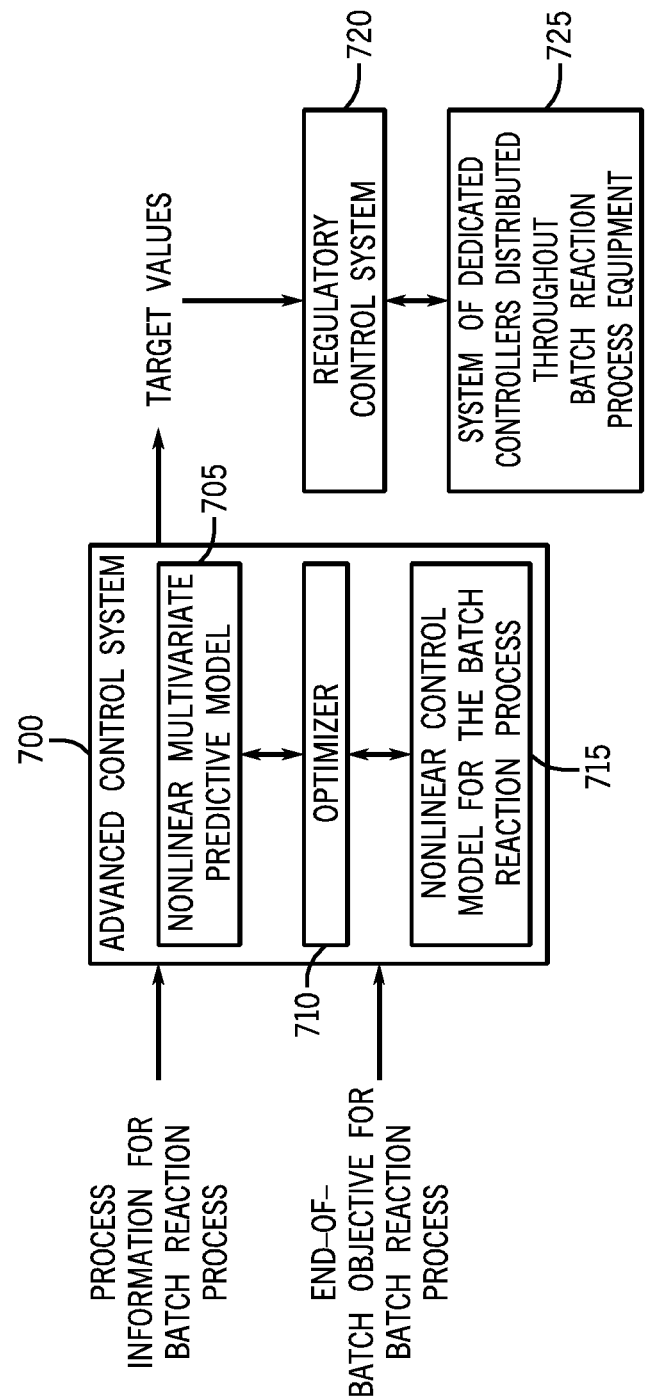
FIG. 7 is a high-level block diagram of a system for managing a batch reaction process of a production process utilizing a nonlinear predictive model and a nonlinear control model.
Figure 8:
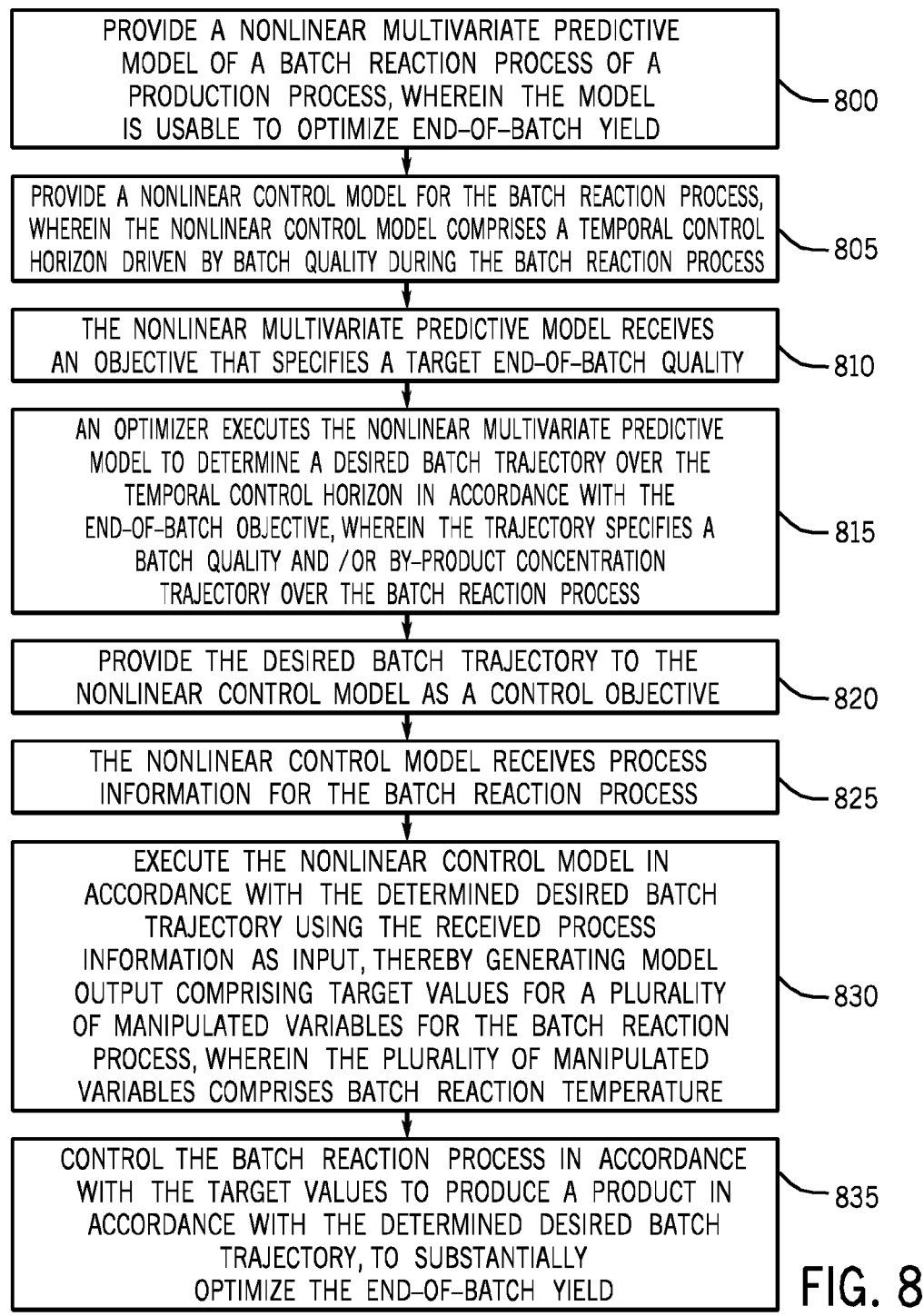
FIG. 8 is a high-level flowchart of a method for managing a batch reaction process of a production process utilizing a nonlinear predictive model and a nonlinear control model.

The following describes preferred embodiments utilizing two nonlinear models to control a batch reaction process of a production process according to the system of FIG. 7 and method of FIG. 8, as well as additional embodiments of model predictive control applied to a batch reaction process. The various systems and methods described use nonlinear models to perform model predictive control to improve the yield, throughput, and/or energy efficiency of the batch reaction process, in accordance with specified objectives. These objectives may be set and various portions of the process controlled substantially continuously to provide real-time control of the production process. The control actions may be subject to or limited by plant and/or external constraints. In the case of a fermentation batch reaction process, an operating objective for the batch reaction process may include operation of the fermentation tanks at an economically optimum targeted fermentation feed rate, i.e., to an economic control objective, and within constraints, such as product quality constraints, process constraints, and/or environmental constraints, among others. Note, however, that the batch reaction process may be other processes of chemical, biochemical, pharmaceutical, water treatment, and other industrial applications.

FIGS. 7 and 8 are directed to control of a batch reaction process in a production process (e.g., the fermentation process 404 in FIG. 4A). More specifically, FIG. 7 is a high-level block diagram of one embodiment of a system, and FIG. 8 is a high-level flowchart of one embodiment of a method for management of the batch reaction process utilizing a nonlinear predictive model and a nonlinear control model to manage end-of-batch objective of the batch reaction process in a production process.

Note that any of the operations and controllable variables of the batch reaction process may be managed or controlled using nonlinear models and/or model predictive control techniques. Below are described various exemplary systems and methods for doing so, although it should be noted that the particular operations and variables discussed are meant to be exemplary, and that any other aspects of the batch reaction process may also be managed using model predictive control as desired.

As shown in FIG. 7, in certain embodiments, a system for management of a batch reaction process of a production process may include an advanced control system 700, including a nonlinear multivariate predictive model 705 (also referred to herein as a nonlinear predictive model) of a batch reaction process of a production process, where the nonlinear multivariate predictive model 705 may be usable to optimize end-of-batch parameters (e.g., yield); and a nonlinear control model 715 for the batch reaction process, where the nonlinear control model 715 includes a temporal control horizon; and a regulatory control system 720, coupled to the advanced control system 700, where the regulatory control system 720 may be operable to be coupled to the batch reaction process of the production process.

The advanced control system 700 may be operable to receive an end-of-batch objective for the nonlinear multivariate predictive model 705, where the end-of-batch objective may specify a target end-of-batch parameter; utilize an optimizer 710 to execute the nonlinear multivariate predictive model 705 to determine a desired batch trajectory over the temporal control horizon in accordance with the end-of-batch objective; provide the desired batch trajectory to the nonlinear control model 715 as a control objective; receive process information for the batch reaction process; and execute the nonlinear control model 715 in accordance with the determined desired batch trajectory using the received process information as input, thereby generating model output including target values for a plurality of manipulated variables for the batch reaction process, where the plurality of manipulated variables includes batch reaction temperature, for example. The regulatory control system 720 may be operable to control the batch reaction process in accordance with the target values to produce a product in accordance with the determined desired batch trajectory to substantially optimize the end-of-batch parameter (e.g., yield).

Embodiments of the model predictive control (MPC) techniques described herein may facilitate this best-case (i.e., optimal or near-optimal) achievement of projected future events, and may also enable multivariate balancing, so that, for example, levels across a series of tanks (e.g., fermentation output holding tanks) may be controlled to achieve optimal or near optimal results within process (and/or other, e.g., economic, regulatory, etc.) constraints even with a transient imbalance due to coordination of batch (e.g., fermentation) and continuous (e.g., stillage) operations. An MPC solution may have relative weighting factors to balance tradeoffs between competing objectives. For example, a tank level may be allowed to swing relatively freely within safe or comfortable operating regions (e.g., a tank level that is not nearly empty or nearing overflow). However, if a tank level forecast estimates that it may be nearly empty or near to over-filling, then different limit weighting may be used to avoid exceeding safe or comfortable operating states.

FIG. 8 is a high-level flowchart of a computer-implemented method for managing a batch reaction process of a production process utilizing nonlinear models and/or model predictive control (MPC), according to one embodiment. In various embodiments, some of the method steps shown may be performed concurrently, in a different order than shown, or may be omitted. Additional method steps may also be performed as desired.

In step 800 of FIG. 8, a nonlinear predictive model for the batch reaction process may be provided. In other words, a model may be provided that specifies or represents relationships between attributes, inputs, and/or other variables of the batch reaction process. Note that the model variables may also include aspects or attributes of other sub-processes that have bearing on or that influence operations of the batch reaction process.

Potential models may be of any of a variety of types. For example, the model may be linear or nonlinear, although for many complex processes, a nonlinear model may be preferred. Other model types contemplated include fundamental or analytical models (i.e., functional physics- or chemistry-based models, also referred to as first-principles models), empirical models (such as neural networks or support vector machines), rule-based models, statistical models, standard MPC models (i.e., fitted models generated by functional fit of data), or hybrid models using any combination of the above models. For example, in certain embodiments where a hybrid approach is used, the dynamic multivariate predictive model may include a fundamental model (e.g., a model based on chemical and/or physical equations) plus one or more of a linear empirical model, a nonlinear empirical model, a neural network, a support vector machine, a statistical model, a rule-based model, or an otherwise empirically fitted model.

A dynamic multivariate predictive model may include a set of process mathematical relationships that includes steady state relationships, and also includes any time lag relationships for each parameter change to be realized. A great variety of dynamic relationships may be possible, and each relationship between variables may characterize or capture how one variable affects another, and also how fast the affects occur or how soon an effect will be observed at another location.

In the case that the batch reaction process is a fermentation process, one embodiment of an MPC-based batch fermentation model may relate changes in batch processing input information (particularly temperature, which may be a critical controllable variable throughout a batch) to biofuel production. Some examples of such input information are provided in the following comments. Yeast addition parameters may include information about both biofuel producing organism quantity (e.g. yeast concentration) and activity. Such information may be measured (frequently in a manually acquired sample tested in a laboratory, although occasionally online by turbidity or optical density measurements that may be related to cell concentrations), inferred from propagation, inferred from mass spectroscopy information on fermentation tank exhaust gas (e.g. oxygen uptake rate, carbon dioxide exhaust rate) or by direct addition information (e.g., values may be obtained from fermentation batches directly inoculated with dried yeast or active yeast slurry), among other techniques. Temperature measurements may be acquired from both the fermentation feed during filling (potentially including liquefaction and/or saccharification temperatures) and a direct measurement of fermentation processing temperature. These temperatures may influence yeast viability, activity, and enzyme activity. Biomass concentration parameters may include the amount of biomass (e.g. yeast nutrient and feedstock amounts available to convert to biofuel) that may be added to the fermentation tank during filling. Acidity, i.e., pH, measurements may include one or more measurements made during the process steps of: liquefaction, saccharification, and/or filling, and/or developing pH values during the batch cycle. Relationships between these pH measurements and yeast viability, production, and enzyme activity may be determined.

While the potential model inputs have influences on many of the critical batch production performance parameters, many of these influences may be independent (e.g. increasing temperature may increase cell death more than growth, even while increasing enzyme activity and nutrition availability to cells). In these relationships, a nonlinear model may be utilized because many of these dependencies may have varied responses at different times during a batch cycle (e.g. cells may become sensitized to higher biofuel concentrations later in a batch cycle, and/or cells may be more temperature tolerant at the beginning of a batch). In addition, enzyme activity, although dependent on temperature may have changing dependencies at varying pH levels.

The complex nature of these biological systems present challenges for model development. In general a more accurate model may provide more complete and accurate relationships between what may be changed (e.g. fermentation temperature, pH, etc.) and what may result from these changes (e.g., biofuel production). Consequently, it may be assumed that a simple model provided with plant operations information (e.g., controller options) may perform better than repeatedly applying the same recipe, e.g., traditional "rules of thumb". Since biomass quality changes, plant operating limits (e.g., equipment capability) change, ambient conditions change, plant economics change (e.g., biomass costs, biofuel costs, processing/energy costs, and by-product demand and costs may change), a fermentation model may perform better if developed with certain methodologies.

An empirical model may be derived directly from past plant performance data, and may represent or encode empirical relationships of the process. There are various ways to develop such a model, but the first priority may be to ensure that non-linear features of the model are based on accurately observed relationships between what may be changed or manipulated and what may result. To achieve such accuracy with empirical modeling, a nonlinear modeling methodology (e.g., artificial neural networks) may provide an advantage. It is rare that such a model can be developed without some plant experimentation, and so either before or during model development, the significant modeled input parameters that can be tested should be tested. Because of the complexity of the described model (e.g., number of potential inputs) the developing may utilize available plant test data and supplement these test data with selective testing on high priority variables, e.g., biomass solids (batch-to-batch), temperature (within several batches), enzyme addition (both batch-to-batch and within several batches) and initial yeast concentrations (batch-to-batch), and so forth.

Exemplary embodiments of the invention may be achieved by addressing certain features by modifying fundamental relationships to provide a kinetic model in the form of modeled equations (relationships), constraints, and definitions, to represent the volumetric change in the fermentation tank, activation rate of yeast, growth rate of yeast, death rate of yeast, conversion rate of sugars, production rate of ethanol, dextrin conversion rate, temperature dependence, and so forth. In general, the form of the equations may be useful for the optimization solutions described herein, and the greatest model uncertainty may be yeast activity. Consequently, a fundamental model may be biased to a measured biofuel production by adjusting a multiplier on the yeast concentration and may be an effective way to adapt fundamental modeling for this application.

In certain embodiments, the fermentation model may be a hybrid combination of the fundamental modeling equations with adjusted parameters (e.g., the parameters of the equations that may be poorly represented in the prior art with respect to currently operated intensive biofuel production). Hybrid or parametric constrained training of empirical modeling may be accomplished with existing empirical modeling, fitting or other techniques, and may be implemented based on historic plant data and limited plant testing data (e.g., a subset of the above variables recommended for testing within the empirical modeling) and used to calculate coefficients as a function of temperature and/or pH.

Hybrid (e.g. combined empirical and fundamental) modeling may use the model equations to calculate various coefficients with available data to fit a best model, within measured and/or historic performance. In general, empirical techniques may be used in this manner to match measured relationships with fundamental equations (e.g., the fundamental literature models were developed from pilot plant experiments). Artificial neural network or other empirical modeling techniques may be used to manage and coordinate data from various sources, limit the identified range of these parameters, and may use nonlinear or linear relationships where appropriate (e.g., where a parameter may be a function of temperature). These tools may be helpful, in development of a fermentation model. The fermentation model may be developed using fundamental, empirical, or a combination of these techniques as described herein.

In certain embodiments, the predictive model may be created from a combination of relationships based on available data such as vessel volumes and fundamental dynamic and gain relationships, sufficiently available and moving plant historic process data, and supplementary plant testing on variables that cannot be identified from the two previous steps. In certain embodiments, the nonlinear multivariate predictive model may be a function of two or more of yeast influence, temperature, biomass concentration, enzyme concentration, batch progress, and/or pH. The yeast influence may include one or more of yeast concentration, yeast addition, or yeast activity, among other yeast-related parameters.

Models may be customized to the plant layout and design, critical inventories, plant constraints and measurements, and controllers available to manage variables. Moreover, in certain embodiments, external factors, such as economic or regulatory factors, may be included or represented in the model. In preferred embodiments, the predictive model may be a nonlinear multivariable predictive model.

An important characteristic of a predictive model may be to identify when a control variable will change as a result of a change in one or more manipulated variables. In other words, the model may identify the time-response (e.g., time lag) of one or more attributes of the fermentation process with respect to changes in manipulated variables. For example, once a controller adjusts pump speeds there may be a certain time-dependent response before observing an effect at a tank being filled. This time-dependent response may be unique for each independent controller (i.e., flow rates may vary because of differences in system variables (e.g., piping lengths, tank volumes, etc.) between the control actuator and flow sensor and the pump location).

In certain embodiments, the predictive model may include inferential models (also referred to as property approximators or virtual online analyzers (VOAs)). An inferential model is a computer-based model that calculates inferred quality properties from one or more inputs of other measured properties (e.g., process temperature(s), flow(s), pressure(s), concentration(s), level(s), etc.). In certain embodiments, the predictive model may be subdivided into different portions, and stored in a plurality of memory media. The memory media may be situated in different locations of the production plant. The controller may communicate with the memory media utilizing a communication system.

In step 805 of FIG. 8, a nonlinear control model (e.g., an optimization-based control model) for the batch reaction process may be provided to utilize MPC to achieve real-time batch adjustment to stay on a quality based trajectory (a trajectory for optimum values of a quality variable throughout a batch) during the batch reaction process. In other words, a nonlinear model may be provided that specifies or represents relationships between attributes, inputs, and/or other variables of the batch reaction process in order to provide continuous (or periodic) batch adjustments to stay on a control variable trajectory provided by the predictive model (e.g., a biofuel concentration trajectory). In particular, the nonlinear control model may include objective functions and constraint sets as described herein. Note that the model variables may also include aspects, attributes, or variables of other subprocesses that have bearing on or that influence operations of the batch reaction process.

There may also be batch reaction process disturbances (not subject to control) that may be unmeasured or even unmeasurable. For example, in a situation where a level starts to rise out of balance with filling demand, e.g., because of manual plant changes (e.g., scheduled equipment cleaning that involves draining and/or filling one or more specific tanks), the control model may be made aware of an imbalance so that corrective actions may be made gradually to avoid dramatic or critical consequences. This may be an issue for many of the tanks that have both batch and continuous plant operations in sequence. Specific tanks may be used to provide storage capacity to facilitate balancing and avoid continuous out-of-control operations after every batch action. Because batch vessels often drain rapidly, specific tank levels may be difficult to maintain in automatic level control. Thus, real-time receipt of current vessel and material balance information (flows and levels) may provide an update on current equipment status and the execution of the dynamic model may enable projections to be made to avoid both emptying/overfilling vessels and emergency large flow moves to correct imbalances.

In certain embodiments, a nonlinear control model may be developed that may manage each batch to the targeted production trajectory (e.g., temperature-dependent or batch-time influence on production). Thus, the nonlinear effect of temperature on production may be common between the model and the controller. From this information, tuned to the plant performance, heat exchanger capacity may be described in past data. Measured, inferred, or off-line modeled qualities may be used to more directly control temperature staging to achieve improved batch reaction results.

In designing such a controller, it may be critical to configure/design a method whereby batch measurements may be received related to production. In general, a real-time controller may have real-time feedback that may inform the control application that it may be performing on the desired trajectory. In this case, the concentration, volume, or mass may not generally be measured in real-time, but may be intermittently sampled by manual operator samples and HPLC results in a production unit laboratory. There may be several solutions for this requirement. First, an online analyzer may be installed and several industrial FT-NIR instruments may meet the requirements of such an analyzer. A second option may be to use the batch reaction models with intermittent feedback, i.e., without real-time feedback, with direct data entry as manual laboratory samples are provided. In this case, the model as incorporated in the controller may run with intermittent feedback (e.g., as when the controller predicts the process response perfectly) until an intermittent data entry occurs. This may be an improvement over current manual control methods performed by an operator, who may make manual temperature adjustments after a number of manual samples indicate that the batch reaction process may need adjustment. In this case, a more comprehensive control model may provide better control through a better defined relationship between production and other variables. In the intermediate case, an inferred property model may be developed using various empirical and fundamental model forms that may provide a more accurate prediction of production than the control model and this may be used in the interim between manual laboratory sampling and data entry to gradually adjust the controller in a feedback basis. In this case, the inferred property model may be using not only input parameters to the controller, but also various state and other process measurement indicators of performance (e.g., cooling water exchanger duty) to more accurately calculate production between manual samples. In this case, when manual samples are taken and made available to the model, the samples may be used to intelligently bias the inferred property model that provides continuous feedback to the controller.

In certain embodiments, a key objective of this controller may be to maintain an optimum production trajectory rather than a temperature staging path. As this may be directly aligned with the objective of the batch reaction process (e.g., biofuel production rather than temperature control), significantly higher performance on each batch, much closer to a consistently best performance, may be achieved. This may occur even under limitations produced by regularly changing processing conditions and economic operating drivers.

In step 810 of FIG. 8, the nonlinear predictive model may receive an objective that specifies a target end-of-batch quality. The specified objective for the batch reaction process may include a desired behavior, attribute, or result of the batch reaction process (e.g., at least one targeted measurable or model-able attribute defining product quality for the batch reaction process output). The objective may be computer generated or input by plant personnel, i.e., the objective for the batch reaction process may be specified by a human operator and/or a program, and may involve a variety of sub-process units in a variety of combinations depending on the specific plant and be subject to a variety of process, equipment, safety and environmental constraints. The objective may impact the product yield, throughput, and/or energy efficiency of the batch reaction process. In certain embodiments, the objective may include one or more sub-objectives. In certain embodiments, the specified objective may be or include an objective function that may specify a set of objective values or relationships corresponding to each of one or more sub-objectives.

In step 815 of FIG. 8, an optimizer may execute the nonlinear predictive model in an iterative manner to determine an optimum batch trajectory over a temporal time horizon in accordance with the end-of-batch objective, wherein the trajectory specifies a batch quality and/or by-product concentration trajectory. The optimizer may be included in, or invoked by, the advanced controller. In various embodiments, any of various optimization techniques may be applied to the above models. For example, in the case of a fermentation process, a model of batch-end ethanol concentration as a function of biomass mass, fermentation temperature staging, enzyme usage, and batch time may be used to calculate biofuel production (e.g., volume or % biofuel) as a gradient or global optimization function to maximize the following equations or a sub-set thereof:

(% Biofuel*Fermenter volume)/(Batch time*Biofuel volumetric cost)

(% Biofuel*Fermenter volume)/(Batch time*Specific processing energy cost)

Biomass mass/(Time*Biomass cost/unit mass)

Enzyme addition/(Time*Enzyme cost/unit added)

In certain embodiments, a more comprehensive optimization approach may be to use a more detailed hybrid model, or any of the above (empirical or fundamental) batch reaction models, to calculate a globally optimum dynamic optimization across possible combinations of batch trajectories. The driving economics may be as straightforward as the above equations or more complex based on more specific options. In the best case, the equations may be constrained by global plant constraints and may be updated in real time or intermittently in real time (limited by CPU capability). However, some optimization methods may be too noisy for real-time optimization, in which case, smoother mathematics, optimization penalties for large unexpected moves, and/or an optimization technique that may be less aggressive (e.g., than genetic algorithms) may be preferred.

In certain embodiments, the dynamic prediction model described above may be incorporated as a process model in a model-based dynamic control system (MPC). The MPC system may project what will happen based on the dynamic prediction model and recent process history. This projection may be updated or biased based on the currently received process information and the control algorithms may be used to recursively estimate the best current and future control moves on the model inputs to achieve a desired output path. Thus, targets set on the dynamic model outputs may be compared to what that output may do over a predictive future horizon and the best available controllable model input moves may be estimated to best achieve the controller targets. In this case, targets on production may be calculated by estimating the best current and future moves regarding batch reaction temperature.

In certain embodiments, the controller or MPC as described above may calculate the future best moves and implement the current moves on each controllable setpoint. In this case, the objective may be a pure reaction balance control system, and many regulatory controllers that deploy the solution may be flow controllers, temperature controllers, or other configured regulatory controllers, that adjust flows (e.g., enzyme flows, cooling water valve positions, or specific controller outputs that may be valve positions for material flow). The current calculated best moves may be written to the regulatory control system (DCS, SCADA, and/or PLC) and these moves may be made to the process.

In certain embodiments, a controllable regulatory controller may be enabled for remote setpoint adjustment, generally with a switch that can be adjusted by plant personnel. If a controller may be an input to the dynamic model above, but disabled from remote setpoint adjustment, it may be assumed independent and measured as feedback from the above receipt of process information. Any controllable input may be calculated and adjusted by changes and communication with parameters in the regulatory control system. This solution may write to these parameters through a control system interface (API) and the control system may implement the changes.

This may be critical because the plant changes and the "best moves" may change from instant to instant or within the execution frequency of the MPC system. If a monitored level changes, or has an offset from the predicted "best" result and control change may be deployed then the best case may be implemented in the plant. This control action frequency may be set up so that many gradual adjustments may be made to provide a stable operating environment. The material flows and temperatures may be relatively stable as compared to manual operation. Ultimately, even with continual, but gradual, adjustments to the process targets, the principal objective may be that yields may be balanced with changing process conditions (e.g., better or worse corn qualities, changing processing limits, and/or yeast activity) so that during the operation of a batch reaction process, there may be a relatively constant yield of product.

In the case of a fermentation process, the recommended methodology may be to use a targeted biofuel concentration (or mass, or volume) trajectory. Controlling the biofuel production and identifying an optimal/best-case trajectory may be the most robust (e.g., flexible, responsive, and reactive) method as batches that require more cooling may be corrected on temperature, while still approaching targeted yields at the targeted batch cycle time. Trajectories may be passed to a dynamic model-based controller either directly as target (or set point) trajectories, so that the controller sees the changing trajectory of the target over the controller's prediction horizon, or at a minimum as a current target only with a frequent update (one fifth of the batch cycle time or faster) to the current target. There may be an advantage to use target trajectories over the control model-prediction horizon (this may be the controller's future prediction time within which target errors may be integrated and minimized by calculated control action). With target trajectories, the current and future targets may be represented within the control horizon, and temperature or other control moves may be made to stay on target as much as possible within this entire prediction window. A single constant target covering multiple hours of increasing biofuel concentration may cause the controller to over- or under-shoot this target trajectory.

In certain embodiments, a second trajectory-based method using constant biofuel concentration may be to limit some other part of the control variable element within a changing trajectory across the batch target. For example, temperature limits may be used based on the dynamic model's forecasted temperature trajectory to achieve substantially optimal biofuel concentration at the end of the batch. In this way a constant, end-of-batch, target biofuel concentration may be used, but temperature (or cooling valve(s)) would be limited so that they do not over-respond to achieve batch targeted responses. A constant temperature limit may not be expected, but one that varies during the batch. This has the disadvantage that batch performance changes may not be evident within the controller and if biofuel production falls behind, something external to the controller may need to change the temperature limits or performance would suffer. In another embodiment, a third approach may be used. Specifically, a fully dynamic batch controller model may be used that calculates and controls to a desired trajectory within the model.

In step 820 of FIG. 8, the desired batch trajectory determined by the optimizer may be provided to the nonlinear control model to be used as a control objective. In other words, the optimizer may execute the nonlinear multivariate predictive model (iteratively) to determine the (substantially) desired batch trajectory per the specified objective (e.g., to maximize end-of-batch biofuel concentration), and this trajectory may then be provided to the nonlinear control model as a control objective.

In step 825 of FIG. 8, process information may be received by the nonlinear control model from the production process. The process information may include measurements of one or more control variables and one or more manipulated variables related to the batch reaction process and one or more variables of other processes that may impact the batch reaction process, and possibly information from inferential models, laboratory results, etc. For example, the process information may include batch temperature, cooling system temperatures, e.g., return broth temperature, cooling water temperature, etc., valve positions, tank volumes or levels, and so forth. The process information may be communicated to the nonlinear control model from a distributed control system.

In certain embodiments, constraint information specifying one or more constraints may also be received. For example, the objective may include constraint information specifying the one or more constraints, i.e., limitations on various aspects, variables, or conditions, related to the batch reaction process, although in other embodiments, the constraint information may be separate and distinct from the specified objective. In certain embodiments, the constraint information may include one or more of a constraint on sugar concentration over the batch fermentation process, or a constraint on end-of-batch sugar concentration.

In certain embodiments, the constraint information may include dynamic constraint information, e.g., the batch reaction process may be controlled in accordance with an objective, but may also be subject to dynamic constraints, e.g., constraints on or of the production facility's equipment, product qualities, its raw material costs, material availability, e.g., water constraints, production plans, product value, product market demand, and other constraints. The nonlinear control model may receive this constraint information specifying one or more constraints related to the batch reaction process, and generate model output in accordance with the objective subject to the one or more constraints.

In certain embodiments, the desired batch trajectory over the temporal control horizon may be determined subject to the at least one constraint. Similarly, the target values for the plurality of manipulated variables may be determined subject to the at least one constraint. Thus, the nonlinear control model may comprise a multivariate predictive model that represents relationships between the one or more constraints, the objective, including any sub-objectives, and the plurality of manipulated variables.

In step 830 of FIG. 8, the nonlinear control model may be executed in accordance with the determined desired batch trajectory using the received process information as input, thereby generating model output (e.g., control decisions) comprising target values for a plurality of manipulated variables related to the batch reaction process, where the plurality of manipulated variables include batch temperature. The target values may correspond to various manipulated variables including, but not limited to, batch fermentation temperature, thin stillage flow rates, and inventories for thin-stillage recycled back to the fermentation units, among others. The nonlinear control model may be configured to generate a plurality of target values for manipulated variables simultaneously.

In certain embodiments, the nonlinear control model and/or the nonlinear multivariate predictive model may be a dynamic model, which may be important because the time response during a batch may be different based on the batch response curve (e.g., typical batch profile for ethanol production). In the case of a fermentation process, the effect of temperature on biofuel production may have complex interactions between the effect on enzyme performance (and nutrient availability) and yeast growth and death. These relationships may not be instantaneous (organisms adapt and become gradually sensitized to conditions) and may dynamically vary (e.g., have different response times) as the batch may be in different phases. The nonlinearities may arise not only from the complex interactions of enzymes and organism relationships to temperature, but also from sensitivity to nutrient and biofuel concentrations (note that the example model presented above uses the well-known fundamental Michaelis-Menten function with Monad kinetics).

Many common significant interactions and model inputs may be represented in the control model, including, for example, temperature, biomass concentration, pH, yeast conditions (activity and concentration), and current biofuel concentration (note that while not an equilibrium equation, the Michaelis-Menten functions may also be an appropriate way to represent the impact of higher ethanol concentrations on slowing batch reaction rates). These relationships, while common in represented form (empirical, fundamental or hybrid) demonstrate several significantly different design and recipe differences, including, for example, simultaneous or series saccharification (with fermentation), yeast propagation with or without aeration, and managing yeast lag phases in different ways to reduce the influence of lags on production, direct yeast addition to fermentation (no propagation) along with more finite changes with yeast strain varieties, (temperature tolerant or high-performance, more sensitive yeasts to yeast hybrids specialized for very high biomass solids concentrations), enzymes, (designed for and with various pH and temperature sensitivities), and fermentations managed with a variety of carbohydrate energy sources (sugar cane, corn, milo, other grains, and cellulose). Thus, there may not be one model common to all biofuel fermentation processes or designs. The dynamic control model may be at least in some way customized or tuned to each fermentation operations' unique process conditions In step 835 of FIG. 8, the batch reaction process may be controlled by the regulatory control system 720 in accordance with the target values to produce a product in accordance with the determined desired batch trajectory, to substantially optimize the end-of-batch yield.

Various aspects of managing the batch reaction process and related portions of other sub-processes in accordance with the target values and the determined desired batch trajectory to provide real-time continuous control of the batch reaction process are presented below. The control actions may be subject to or limited by plant and external constraints. More specifically, various embodiments of the invention may be utilized to control one or more aspects of the batch reaction process and related portions of other sub-processes, including, but not limited to, one or more of: (1) feed rate to the fermentation tanks, (2) energy requirements in the chillers, (3) feed rate of recycled water from the primary distillation tower units to the fermentation tanks, and (4) feed rate of thin stillage to the fermentation process (also referred to as recycle % or backset recycle streams).

In certain embodiments, controlling flow rates of fermentation feed to each fermentation tank by the regulatory control system 720 may involve one or more of: one or more flow controllers coupled to fermentation feeds to each fermentation tank, level sensors for one or more fermentation feed holding tanks, and/or flow sensors to measure feed rate to each of the fermentation tanks. In certain embodiments, the system may include an energy center and MPC control may be used to control the energy utilization efficiency for the batch fermentation process by regulating the energy demand. In another embodiment, MPC may be configured to control the energy center subject to environmental requirements. In certain embodiments, controlling the biofuel production process may include control of the inventory of biofuel, which may include or utilize one or more of: a measure of the inventory of one or more biofuel products, an operator or computer entered control objective for the inventory of one or more biofuel products.

In certain embodiments, the control model may be used in a model-based controller that uses this model-based process to target specific best-case plant performance. As biofuel concentrations (or volume, mass) change dynamically (but not instantaneously) after changes in fermenter environment (volume, concentrations, enzymes, temperature, pH), a model-based controller may predict in real-time, not only how far, but how fast temperature or other fermenter controllers should be adjusted to move operations from current performance to target concentrations. The accuracy of the model with respect to the process (and the biofuel concentration measurement) may avoid corrections based on model error and may limit controller course corrections (e.g. batch trajectory) to those that may be real rather than course corrections that may be based on model mismatch. So while any robust controller algorithm may perform reasonably well even with model mismatch, reducing this mismatch may enable more aggressive controller action and therefore tighter control to the targeted (best) batch trajectory.

In certain embodiments, a robust control algorithm may be used (e.g., to control the batch reaction process). For example, any of various nonlinear control methodologies may be used, ranging from fairly frequent linear model corrections (e.g., gain scheduling (e.g., within one fifth to one tenth of a batch cycle)), to similar active controller switching (e.g., using linear controllers operating in parallel, whose results may be selected based on batch conditions) to fully nonlinear controllers of various architectures. Adaptive control may be feasible although it may be assumed that the primary model adaptation may be identified off-line and automatically adapted based on batch progression with an ability to refine any nonlinear model with adaptation as an added feature within the construct of a fairly representative batch nonlinear control model (e.g., current adaptive control model technology may be assumed to be too slow to manage the fairly continuously changing batch interactions described under the dynamic model sections described above).

Assuming that model accuracy may be relative, and that a robust control model algorithm may be used (e.g. the controller may be designed to live with and manage control within certain amounts of model uncertainty and error), dynamic control model accuracy improves performance, but may provide satisfactory batch reaction control improvements across a range of sophistication and accuracy. Control model accuracy may be the ultimate delivery mechanism of performance improvements and it may need to be sufficiently accurate to enable improved response beyond current manual operations ability within the limitations of their understanding and in this case the available amount of time to pay attention to the batch reaction process.

As noted above, in certain embodiments, MPC may allow not only this best case achievement of projected future events, but may also enable multivariate balancing so that, for example, in the case where temperature affects both yeast growth, death rates, and nutrient availability, the yeast produces ethanol as a function of temperature, nutrient level, and biofuel concentration the nonlinear interactions and therefore the "right" temperature moves may be somewhat complex. Finally, there may be in addition, complex interactions between temperature and enzyme activity with differing relationships between yeast activity and temperature. The trade-offs of enzyme addition and temperature staging may be most readily handled in a multivariate control solution. In such a solution, these interactions may be solved as part of the model and the best approach to the biofuel production target may be made.

Various method steps of the method of FIG. 8 may be repeated, e.g., at a specified frequency, or in response to specified events, so that the batch reaction process may be monitored and controlled throughout a production process, or throughout a series of production processes. For example, in certain embodiments, the above receiving process information, executing the nonlinear control model, and controlling, may be repeated in an iterative manner to achieve targeted production over a batch. In certain embodiments, the repeating the executing the nonlinear control model may generate target values comprising a temperature staging profile for the batch.

In certain embodiments, the period or frequency may be programmed or varied during the production process (e.g., an initial portion of a production process may have longer repetition periods (lower frequency), and a critical portion of a production process may have shorter repetition periods (higher frequency)). As mentioned above, in certain embodiments, the repetition may be based at least partially on events (e.g., in response to specified conditions). In certain embodiments, the receiving an objective may also be included in the repeating. In other words, the receiving an objective, receiving process information, executing the dynamic multivariate predictive model, and controlling the production process may be repeated with a specified frequency (or in response to specified events or conditions), utilizing updated process information and objectives in each repetition. The frequency may be programmable, and/or operator-determined as desired. In certain embodiments, the frequency may be determined by changes in process, equipment, regulatory, and/or economic constraints.

In certain embodiments, a key benefit comes from automatically using this dynamic model information to control each batch (e.g. each of several active batches active at any one moment in time at various stages of completion) to its best-case target. This may be accomplished by running the control model calculations in parallel to the process, updating its status as frequently as possible, including updating model inputs (e.g., temperature, cooling demand, pH, yeast addition, biomass concentration, etc.) and model outputs (e.g., biofuel concentration, concentrations of sugars) at the slowest frequency of the controller execution frequency or the controller input update frequency.

In certain embodiments, the executed control model may make real-time changes throughout a batch to regularly correct the batch production path to the target. This may result in continuous performance that approaches the target and automatically assure substantially best-case results. Additionally, after managing a good series of batches at high performance the opportunity to execute the dynamic model at even better levels of performance may become evident. If, for example, increasing temperature to a maximum during some phase of the batch is a significant part of the highest batch performance, tests can be run at even higher levels (e.g. by several tenths of a degree) to determine whether higher performance is possible. In addition, it may be fairly straightforward to use slightly higher trajectories over the entire batch (e.g., increase the trajectory by 0.5%*batch time/total batch cycle time) to check if the controller can find a path to an additional 0.5% yield.

In certain embodiments, the use of dynamic inferred properties may be preferred. For example, the better the inferred property model relationship to the process relationships that may be measured, the higher the trust factor in the model and the further batch reaction process performance can be performed. In the event that an online analyzer can provide real-time feedback to the described control model system, a separate inferred property model may or may not be required. In most cases, it may be useful to have a separate inferred property model because the control model represents, in most cases, the nonlinear gain and dynamic relationships although does not use state and indirect measured properties that support the inferred property model. These can be used to improve the accuracy of the inferred property model, but can misdirect the control model. In any event, a dynamic inferred property model improves accuracy because if temperature changes may be in process of being made only part of the response has occurred and to synchronize the measurement at any point (e.g. model verification and biasing) a better model provides a better match and enables a more aggressive biasing and in most cases less significant biasing.

Certain aspects of the model predictive control techniques described above may be found in U.S. Patent Application Publication No. 2008/0109100 to Macharia et al., and U.S. Patent Application Publication No. 2008/0167852 to Bartee et al., each of which is incorporated by reference in its entirety.

In general, the first step in developing a model predictive control solution is to identify and develop an appropriate process model. Because of the additional complexity of batch reaction systems, the hybrid techniques described herein provide unique advantages. Hybrid techniques leverage known fundamental batch relationships (known kinetic models, growth models, and so forth) that are more or less available from fundamental process modeling with empirical modeling techniques for process phenomena not accurately modeled due to a lack of fundamental understanding. Because industrial-scale process equipment is generally uniquely designed and developed for intensive process operations, significant calibration or tuning of published or available fundamental modeling with specifically-designed empirical modeling techniques provides more accurate process models. In turn, a more accurate process model enables a more highly performing model-based control solution.

Therefore, an ideal modeling solution incorporates the best available fundamental process models and empirical models tuned or calibrated to best match collected process measurement/performance data over varying operating phases of the batch reaction process. Depending on the accuracy of the hybrid solution, either constant (e.g. single value) parameters or varying (e g kinetic parameters that vary in the course of batch operation, for example as a linear or nonlinear function of measured batch properties) parameters can be identified and used.

Figure 9:
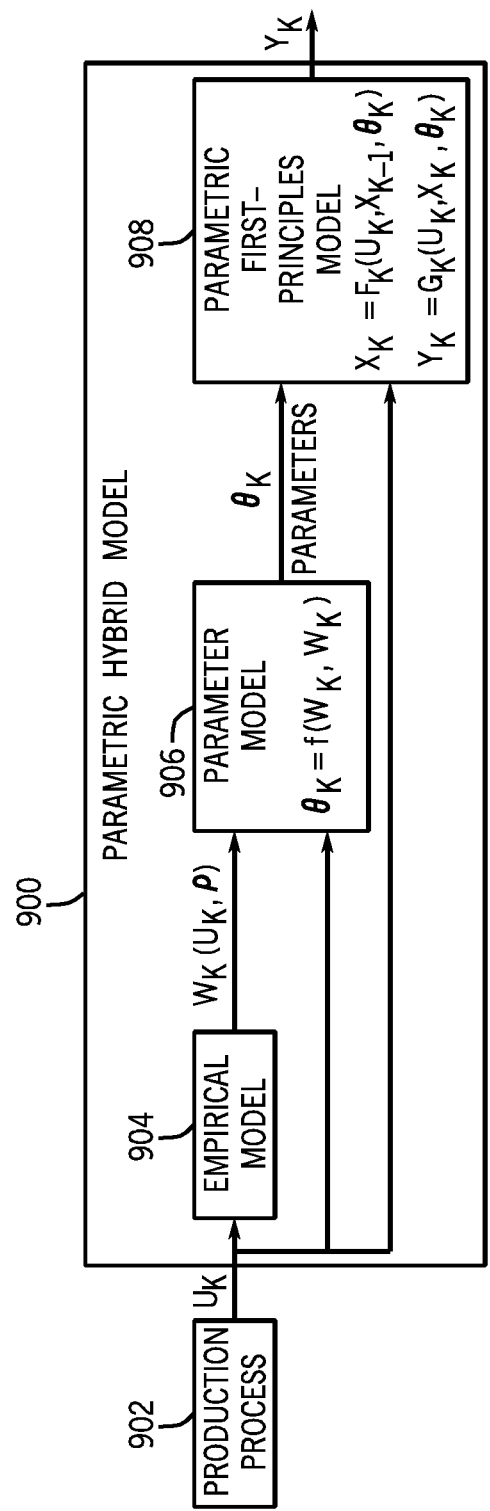
FIG. 9 is a schematic diagram of an exemplary parametric hybrid model for modeling a batch reaction process.

FIG. 9 is a schematic diagram of an exemplary parametric hybrid model 900 for modeling a batch reaction process. In certain embodiments, the parametric hybrid model 900 may be part of the dynamic multivariate predictive model 602 of FIG. 6A and/or the nonlinear multivariate predictive model 705 of FIG. 7. As illustrated, production process inputs $u_k$ from the production process 902 may be received by the parametric hybrid model 900. An empirical model 904 may use the production process inputs $u_k$ to generate empirical model outputs $w_k$. The empirical model outputs $w_k$ may be a function of the production process inputs $u_k$ and the empirical model parameters $\rho$. Both the empirical model outputs $w_k$ and the production process inputs $u_k$ may be directed into a parameter model 906 of the parametric hybrid model 900. Fundamental model parameters $\theta_k$ from the parameter model 906 may be a function of the production process inputs $u_k$ and the empirical model outputs $w_k$. In certain embodiments, the fundamental model parameters $\theta_k$ may include the empirical model outputs $w_k$, or may simply be identical to the empirical model outputs $w_k$ in their simplest form. The fundamental model parameters $\theta_k$ may be directed into a parametric first-principles model 908, which may be either a steady-state or dynamic model. In addition, the parametric first-principles model 908 may receive the production process inputs $u_k$ from the production process 902. The parametric first-principles model 908 may model measured or unmeasured production process state variables $x_k$ and production process outputs $y_k$. The production process state variables $x_k$ may be a function of the production process inputs $u_k$, previous production process state variables $x_k$, and the fundamental model parameters $\theta_k$. The production process outputs $y_k$ may be a function of the production process inputs $u_k$, current production process state variables $x_k$, and the fundamental model parameters $\theta_k$. The production process outputs $y_k$ may be directed from the parametric hybrid model 900 as process outputs. Therefore, the general equations defining the parametric hybrid model 900 include:

$$w_k = f_1(u_k, \rho)$$

$$\theta_k = f_2(u_k, w_k)$$

$$x_k = F_k(u_k, x_{k-1}, \theta_k)$$

$$y_k = G_k(u_k, x_k, \theta_k)$$

where $u_k$ is a vector of process inputs over time k, $\rho$ is a vector of empirical model parameters, $w_k$ is a vector of empirical model outputs over time k, $\theta_k$ is a vector of fundamental model parameters over time k, $x_k$ is a vector of measured or unmeasured production process state variables over time k, and $y_k$ is a vector of production process outputs over time k.

The parametric hybrid model 900 is extremely efficient for real-time optimization and control computations. This computational efficiency is critical to the successful implementation of a model-based control strategy that optimizes the performance of a batch reaction system. For a fed-batch model, as opposed to a mixed-batch model, the reaction/production occurs not only at a fixed, final volume, but also during the reactor filling, once initiation has occurred. In this event, ingredients may be added at varying ratios during filling so that concentrations within the batch vessel are integrated during the filling of the batch vessel, in addition to any reactions occurring during the fill that change concentrations. Once filled, the contents of the reaction vessel are relatively constant and batch reactions change vessel concentrations. Taking all this into consideration, the embodiments described herein work equally well for both mixed-batch and fed-batch reaction systems.

One objective of the model predictive control techniques described above is to minimize economic or target objectives over a dynamic time horizon, but with each point in the time horizon being treated identically. For example, this implies that in a situation where moisture in a dried product is controlled using a one-hour prediction horizon, errors in moisture are integrated over the one hour and controller actions are calculated to minimize offset of this error over the horizon (e.g., the entire hour). If the production rate is maximized, it is continuously maximized to produce the most product over the hour-long time horizon. However, in a batch reaction system, the production rate half-way through the batch is irrelevant, except inasmuch as it affects the end-of-batch production quantities and/or qualities. In certain situations, at the end of the batch reaction process, the reaction is terminated and the production volume may be further purified to extract the product from other reaction residue, by-product, or residual feedstock. As such, dynamic optimization of batch reaction processes is based only on maximizing end-of-batch production, which is different from maximizing production rates at every time period during a batch reaction process. Therefore, the model predictive control algorithms and optimization routines described above may be modified to calculate desired batch trajectories either within or separate from the real-time control system.

Whereas continuous process optimization may consider steady-state operations and extract production value and costs over any given time period, batch process optimization may consider each batch (and the time the batch takes to process) as an optimization segment and optimize end-of-batch production value versus the costs to create the end-of-batch product. This type of batch optimization occurs independent of any interim batch production, because only the product that is extracted to be sold is relevant. However, as described herein, dynamic optimization methods are used to calculate optimal dynamic trajectories during the batch process to create the highest batch performance possible. In particular, a batch performance trajectory is optimized to a target over time or batch progression based on quality parameters that closely relate to, but are not the same as, the ultimate process objectives. More specifically, as illustrated in FIG. 9, the fundamental model parameters $\theta_k$ generated by the parameter model 906 may be a set of parameters that are not directly analogous to either the production process inputs $u_k$ or the production process outputs $y_k$. Rather, certain derived measures of batch reaction processes (e.g., the parameters) over the course of the batch reaction progression may be used to generate continuous trajectories that strongly correlate to batch performance criteria, even when the performance criteria are defined for the end-of-batch only. In particular, high fidelity models of end-of-batch quality measurements may be generated using measured variables during the batch. For example, in a pharmaceutical production process, total feed, maximum variations in the content of poison in the broth, broth pH levels, maximum rate of change in the batch pH level, and so forth, may be used to predict end-of-batch quality measurements, such as Titer concentrations.

For example, if a batch polymer (e.g. PVC) reaction is progressing, the polymer growth progression, average chain-length, or viscosity would be more closely correlated to end-of-batch polymer qualities than would reactor temperature. However, reactor temperature may be measured (even intermittently) directly or indirectly, and as such may be an ideal trajectory target. Therefore, this critical batch quality parameter may be calculated over the duration of the batch with the batch models described above calculating the optimal quality trajectory. This allows better real-time control during a batch reaction process such that intermediate batch performance may be more closely targeted and maintained. In certain embodiments, the optimal trajectory function may be determined by solving:

$$\min(u_k) \Gamma(\hat{y}_k, \hat{y}_k^{Trajectory}) \text{ subject to:}$$

$$w_k = f_1(u_k, \rho)$$

$$\theta_k = f_2(u_k, w_k)$$

$$x_k = F_k(u_k, x_{k-1}, \theta_k)$$

$$y_k = G_k(u_k, x_k, \theta_k)$$

$$L < u_k < H$$

where $\theta()$ is the objective function defined over measured or modeled process outputs, $\hat{y}_k$ is the measured or modeled process outputs ($\hat{y} \in y$), and $\hat{y}_k^{Trajectory}$ is an explicit or implicit representation of a desired process trajectory. As an example, the objective function can be constructed incorporating items such as described below:

$$(\Sigma \text{Price batch product} * \text{Batch volume} * \text{End-of-batch concentration} +$$
$$\Sigma \text{ Price of batch co-product} * \text{Batch volume} * \text{End-of-batch}$$
$$\text{co-product conc.} - \Sigma \text{ Cost of feedstock} * \text{Feedstock volume}$$
$$\text{integrated over batch} - \Sigma \text{ Cost of catalysts, enzymes,}$$
$$\text{other ingredients} * \text{Volumes integrated over batch} - \Sigma \text{ Cost of}$$
$$\text{utilities} * \text{Quantities of utilities integrated over batch}) / \text{Batch Time}$$

The minimization of the above objective function is achieved through adjustments to the decision variables $u_k$ (e.g., the batch variable inputs). Note that the optimization problem above is merely exemplary and not intended to be limiting. For example, the objective function $\Gamma(\ )$ may be defined to include penalties on decision variables $u_k$.

In addition, constraints (e.g., L and H above) may be incorporated as trajectory function, including both real-time and end-of-batch limits (e.g. maximum/minimum utility consumption, temperatures within equipment or reaction limits, and maximum/minimum co-product or contaminant concentrations in the end-of-batch volume). Within these constraints, and to maximize the above objective function, a series of manipulated variables may be adjusted, including time-varying elements that may be varied throughout the batch operation or within phases of the batch operation, and single variables that may be adjusted once (e.g., total volume of an initiator, catalysts, or enzymes added to the start of a batch cycle).

The dynamic optimization described above may be implemented using various methods. The level of detail included in the parametric hybrid model 900 may vary depending upon the level of complexity that may be handled in real time. In other words, the parametric hybrid modeling allows a systematic way of compromising between model accuracy and computational complexity and, therefore, offers flexibility to handle batch systems of varying levels of complexity. More specifically, the complexity of any given parametric hybrid model is a function of both the complexity of the system being modeled, and the simplicity of the parametric hybrid model needed to make real-time computations tractable. As such, the parametric hybrid model framework offers a systematic framework for optimally trading off model accuracy versus computational efficiency. In defining parametric hybrid models, in certain embodiments, short-cut models may be used (e.g., in the parametric first-principles model 908). These short-cut models may be linear or nonlinear, dynamic or steady-state, and so forth. The parametric hybrid model framework remains current with the real-time operating conditions of the batch process, and allows for online modification of the model parameters, which are not direct inputs or outputs of the system, and hence the decision engine (i.e., the optimization and control) always has valid models upon which to base decisions.

The parametric hybrid model 900 models both steady-state and the non-steady-state behavior of the batch process, whether the behavior is linear or nonlinear, with respect to critical variables, where gains and/or dynamics may vary during operation of the system. Some of the variables (e.g., the parameters described herein) that are indicative of performance of the batch process may not be measured or even easily measurable. The parametric hybrid model 900 is used to model these variables as well. Then, an optimizer may make decisions as to which inputs to the batch process should be manipulated, given system models/objectives/constraints.

As such, the parametric hybrid model framework allows all of the models to remain current, while solving the optimization problem (i.e., making decisions) as quickly as possible. Achieving these two goals enables the batch control system described herein to continuously make the best decisions based on what is actually happening with the batch process in real-time, even if performance objectives are only defined at the end of the batch. The ability to create a continuous measure of performance/constraint that properly correlates with the end-of-batch performance/constraint is a key feature of this invention.

Therefore, the disclosed embodiments are directed to tracking quality parameters that are closely related to, but not identical to, end-of-batch objectives during the progression of a batch reaction process, and using these quality parameters to correct the batch trajectory while the batch is still progressing. This is most beneficial in cases where the end-of-batch property is not easily measurable during the batch reaction process, either directly or indirectly. The disclosed embodiments incorporate the parametric hybrid model 900 of FIG. 9, which includes the parametric first-principles model 908 and the empirical model 904 parameterized with data collected from the production process 902.

Figure 10:
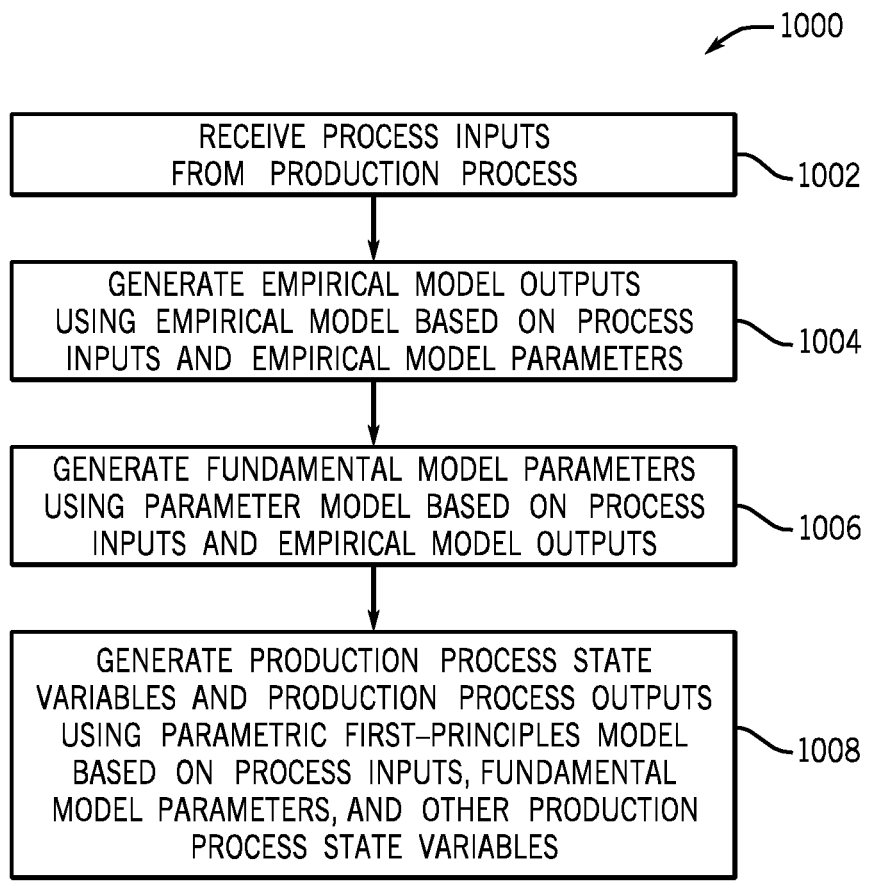
FIG. 10 is a high-level flowchart of a method of implementing the parametric hybrid model of FIG. 9.

More particularly, FIG. 10 is a high-level flowchart of a method 1000 of implementing the parametric hybrid model 900 of FIG. 9. In step 1002, production process inputs $u_k$ may be received by the parametric hybrid model 900 from the production process 902. In particular, many of the production process inputs $u_k$ may be related to the batch reaction process of the production process 902. However, the production process inputs $u_k$ may also include variables related to other sub-process of the production process 902. In step 1004, the empirical model 904 may generate empirical model outputs $w_k$, which are a function of the production process inputs $u_k$ from the production process 902 and empirical model parameters $\rho$. In step 1006, the parameter model 906 may generate fundamental model parameters $\theta_k$, which are a function of the production process inputs $u_k$ from the production process 902 and the empirical model outputs $w_k$ from the empirical model 904. In step 1008, the parametric first-principles model 908 may generate production process state variables $x_k$ and production process outputs $y_k$. The production process state variables $x_k$ may be a function of the production process inputs $u_k$, previous production process state variables $x_k$, and the fundamental model parameters $\theta_k$. The production process outputs $y_k$ may be a function of the production process inputs $u_k$, current production process state variables $x_k$, and the fundamental model parameters $\theta_k$. It should be understood that the steps 1002, 1004, 1006, 1008 of the method 1000 may be performed consecutively, iteratively, in any particular order, or in any other manner enabled by the parametric hybrid model 900.

As such, the parametric hybrid model 900 models both steady-state and non-steady-state batch reaction processes of the production process 902 in a nonlinear and/or linear manner with respect to critical process variables, where process gains and/or dynamics may vary over the batch reaction process progression. The parametric hybrid model 900 is used to generate continuous trajectories for "derived" measures (e.g., parameters) of batch reaction operation over the course of the batch reaction progression. The continuous trajectories will strongly correlate to batch reaction performance criteria, even when the performance criteria are defined for the end-of-batch only. The parametric hybrid model 900 enables the abstraction of the time axis from the batch reaction models, which have long been considered indispensable in the modeling of batch reaction processes. The parametric hybrid model 900 is then used to calculate an optimal dynamic trajectory or batch reaction path based on the critical quality parameters. The critical quality parameters are measured or estimated parameters that correlate well with, but are not the same as, ultimate batch objectives (e.g., optimal end-of-batch production of some chemical or biological agent). Then, the dynamically-generated optimal trajectory and the parametric hybrid model 900 may be incorporated into a real-time, model-based control system that corrects batch progression as closely as possible, following the optimal quality parameter trajectory within equipment constraints. As such, performance of the batch reaction process is maximized with respect to an end-of-batch quality, production, yield, efficiency, profitability, or some combination of these objectives.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for managing a batch fermentation reaction process of a biofuel production process, comprising:
   (a) providing, to a computer-based controller, a parametric hybrid model of a batch fermentation reaction process of a biofuel production process for optimizing a continuous quality objective and an end-of-batch quality objective, where the continuous quality objective is an output of the parametric hybrid model that correlates to the end-of-batch quality objective, and the end-of-batch quality objective comprises a yield of a biofuel product, a throughput of the biofuel product, or an energy efficiency of the batch fermentation reaction process, and determining an optimal batch trajectory over a predictive future control horizon in accordance with the continuous quality objective and the end-of-batch quality objective based at least in part on batch fermentation reaction process information received during a cycle of the batch fermentation reaction process, wherein the parametric hybrid model comprises an empirical model for generating empirical model outputs based at least in part on the batch fermentation reaction process information, a parameter model for generating fundamental model parameters based at least in part on the batch fermentation reaction process information and the empirical model outputs, and a parametric first principles model for generating the continuous quality objective and the end-of-batch quality objective based at least in part on the batch fermentation reaction process information and the fundamental model parameters, wherein the fundamental model parameters represent operating variables that relate to, but are not the same as, inputs and outputs of the batch fermentation reaction process;
   (b) automatically modifying the parameters of the parametric hybrid model using the parameter model of the parametric hybrid model based on changing operating conditions of fermentation tanks and chillers of the batch fermentation reaction process of the biofuel production process that are monitored by one or more sensors, wherein the operating conditions comprise temperatures, pressures, flow rates, equipment settings, or a combination thereof;
   (c) providing, to the computer-based controller, objective functions and constraint sets for optimization-based control of the batch fermentation reaction process;
   (d) providing, to the computer-based controller, the determined optimal batch trajectory;
   (e) executing, in the computer-based controller, the optimization-based control model using the automatically modified parameters of the parametric hybrid model in accordance with the determined optimal batch trajectory, the objective functions and constraint sets, and the batch fermentation reaction process information, thereby generating control decisions comprising target values for a plurality of manipulated variables for the batch fermentation reaction process; and
   (f) controlling, using the computer-based controller, operating variables of the batch fermentation reaction process during the cycle of the batch fermentation reaction process in accordance with the target values to produce a biofuel product in accordance with the determined optimal batch trajectory, wherein the operating variables comprise catalyst influence, temperature, feedstock ingredient concentration, enzyme concentration, batch progress, or pH.

2. The method of claim 1, wherein the end-of-batch quality objective comprises an end-of-batch yield.

3. The method of claim 1, wherein the plurality of manipulated variables comprise catalyst influence, temperature, feedstock ingredient concentration, enzyme concentration, batch progress, or pH.

4. The method of claim 1, wherein the determined optimal batch trajectory specifies a batch quality and/or by-product concentration trajectory during the batch fermentation reaction process.

5. The method of claim 1, comprising receiving at least one by-product concentration constraint at the computer-based controller, comprising one or more of:
   a first by-product concentration constraint on by-product concentration over the cycle of the batch fermentation reaction process; or
   a second by-product concentration constraint on end-of-batch by-product concentration.

6. The method of claim 5, wherein the determined optimal batch trajectory over the predictive future control horizon is determined subject to the at least one by-product concentration constraint.

7. The method of claim 5, wherein the target values for the plurality of manipulated variables are determined subject to the at least one constraint.

8. The method of claim 1, comprising repeating steps (b)-(f) in an iterative manner to achieve targeted biofuel production over a plurality of cycles of the batch fermentation reaction process.

* * * * *